United States Patent
Bozko (10) Patent No.: US 9,805,257 B1
(45) Date of Patent: Oct. 31, 2017

(54) PRINTER METHOD AND APPARATUS

(71) Applicant: Datamax-O'Neil Corporation, Orlando, FL (US)

(72) Inventor: Dmitriy Sergeevich Bozko, Mission Viejo, CA (US)

(73) Assignee: Datamax-O'Neil Corporation, Orlando, FL (US)

( * ) Notice: Subject to any disclaimer, the term of this patent is extended or adjusted under 35 U.S.C. 154(b) by 0 days.

(21) Appl. No.: 15/258,483

(22) Filed: Sep. 7, 2016

(51) Int. Cl.
G06K 9/78 (2006.01)
G06K 9/00 (2006.01)
G06K 9/20 (2006.01)
G06Q 20/20 (2012.01)
G06K 9/22 (2006.01)

(52) U.S. Cl.
CPC ..... *G06K 9/00449* (2013.01); *G06K 9/00442* (2013.01); *G06K 9/2054* (2013.01); *G06K 9/222* (2013.01); *G06Q 20/208* (2013.01)

(58) Field of Classification Search
CPC .......... G06K 9/00449; G06K 9/00442; G06K 9/222; G06K 9/2054; G06Q 20/208
USPC ....................................................... 347/232
See application file for complete search history.

(56) References Cited

U.S. PATENT DOCUMENTS

| | | | |
|---|---|---|---|
| 5,524,993 A | 6/1996 | Durst | |
| 6,010,257 A | 1/2000 | Petteruti et al. | |
| 6,348,697 B1 * | 2/2002 | Kitajima | B65H 7/14 250/559.4 |
| 6,832,725 B2 | 12/2004 | Gardiner et al. | |
| 7,128,266 B2 | 10/2006 | Zhu et al. | |
| 7,159,783 B2 | 1/2007 | Walczyk et al. | |
| 7,413,127 B2 | 8/2008 | Ehrhart et al. | |
| 7,726,575 B2 | 6/2010 | Wang et al. | |
| 8,294,969 B2 | 10/2012 | Plesko | |
| 8,317,105 B2 | 11/2012 | Kotlarsky et al. | |
| 8,322,622 B2 | 12/2012 | Liu | |
| 8,366,005 B2 | 2/2013 | Kotlarsky et al. | |
| 8,371,507 B2 | 2/2013 | Haggerty et al. | |

(Continued)

FOREIGN PATENT DOCUMENTS

| | | |
|---|---|---|
| WO | 2013163789 A1 | 11/2013 |
| WO | 2013173985 A1 | 11/2013 |

(Continued)

OTHER PUBLICATIONS

U.S. Appl. No. 14/715,916 for Evaluating Image Values filed May 19, 2015 (Ackley); 60 pages.

(Continued)

*Primary Examiner* — Huan Tran
*Assistant Examiner* — Alexander D Shenderov
(74) *Attorney, Agent, or Firm* — Additon, Higgins & Pendleton, P.A.

(57) ABSTRACT

A printer has a light source that directs light toward a print medium path. An RGB sensor is positioned to receive light from the light source that is reflected by the print medium. An infrared light filter is situated between the RGB sensor and the paper to filter out infrared light. A programmed processor is coupled to an output of the RGB sensor in order to detect form elements in the output from the RGB light sensor, retrieve a stored electronic representation of a form, match the form elements to the stored electronic representation of the form to identify locations on the form, and control printing to the form.

20 Claims, 5 Drawing Sheets

(56) References Cited

U.S. PATENT DOCUMENTS

| | | |
|---|---|---|
| 8,376,233 B2 | 2/2013 | Van Horn et al. |
| 8,381,979 B2 | 2/2013 | Franz |
| 8,390,909 B2 | 3/2013 | Plesko |
| 8,408,464 B2 | 4/2013 | Zhu et al. |
| 8,408,468 B2 | 4/2013 | Van Horn et al. |
| 8,408,469 B2 | 4/2013 | Good |
| 8,424,768 B2 | 4/2013 | Rueblinger et al. |
| 8,448,863 B2 | 5/2013 | Xian et al. |
| 8,457,013 B2 | 6/2013 | Essinger et al. |
| 8,459,557 B2 | 6/2013 | Havens et al. |
| 8,469,272 B2 | 6/2013 | Kearney |
| 8,474,712 B2 | 7/2013 | Kearney et al. |
| 8,479,992 B2 | 7/2013 | Kotlarsky et al. |
| 8,490,877 B2 | 7/2013 | Kearney |
| 8,517,271 B2 | 8/2013 | Kotlarsky et al. |
| 8,523,076 B2 | 9/2013 | Good |
| 8,528,818 B2 | 9/2013 | Ehrhart et al. |
| 8,544,737 B2 | 10/2013 | Gomez et al. |
| 8,548,420 B2 | 10/2013 | Grunow et al. |
| 8,550,335 B2 | 10/2013 | Samek et al. |
| 8,550,354 B2 | 10/2013 | Gannon et al. |
| 8,550,357 B2 | 10/2013 | Kearney |
| 8,556,174 B2 | 10/2013 | Kosecki et al. |
| 8,556,176 B2 | 10/2013 | Van Horn et al. |
| 8,556,177 B2 | 10/2013 | Hussey et al. |
| 8,559,767 B2 | 10/2013 | Barber et al. |
| 8,561,895 B2 | 10/2013 | Gomez et al. |
| 8,561,903 B2 | 10/2013 | Sauerwein, Jr. |
| 8,561,905 B2 | 10/2013 | Edmonds et al. |
| 8,565,107 B2 | 10/2013 | Pease et al. |
| 8,571,307 B2 | 10/2013 | Li et al. |
| 8,579,200 B2 | 11/2013 | Samek et al. |
| 8,583,924 B2 | 11/2013 | Caballero et al. |
| 8,584,945 B2 | 11/2013 | Wang et al. |
| 8,587,595 B2 | 11/2013 | Wang |
| 8,587,697 B2 | 11/2013 | Hussey et al. |
| 8,588,869 B2 | 11/2013 | Sauerwein et al. |
| 8,590,789 B2 | 11/2013 | Nahill et al. |
| 8,596,539 B2 | 12/2013 | Havens et al. |
| 8,596,542 B2 | 12/2013 | Havens et al. |
| 8,596,543 B2 | 12/2013 | Havens et al. |
| 8,599,271 B2 | 12/2013 | Havens et al. |
| 8,599,957 B2 | 12/2013 | Peake et al. |
| 8,600,158 B2 | 12/2013 | Li et al. |
| 8,600,167 B2 | 12/2013 | Showering |
| 8,602,309 B2 | 12/2013 | Longacre et al. |
| 8,608,053 B2 | 12/2013 | Meier et al. |
| 8,608,071 B2 | 12/2013 | Liu et al. |
| 8,611,309 B2 | 12/2013 | Wang et al. |
| 8,615,487 B2 | 12/2013 | Gomez et al. |
| 8,621,123 B2 | 12/2013 | Caballero |
| 8,622,303 B2 | 1/2014 | Meier et al. |
| 8,628,013 B2 | 1/2014 | Ding |
| 8,628,015 B2 | 1/2014 | Wang et al. |
| 8,628,016 B2 | 1/2014 | Winegar |
| 8,629,926 B2 | 1/2014 | Wang |
| 8,630,491 B2 | 1/2014 | Longacre et al. |
| 8,635,309 B2 | 1/2014 | Berthiaume et al. |
| 8,636,200 B2 | 1/2014 | Kearney |
| 8,636,212 B2 | 1/2014 | Nahill et al. |
| 8,636,215 B2 | 1/2014 | Ding et al. |
| 8,636,224 B2 | 1/2014 | Wang |
| 8,638,806 B2 | 1/2014 | Wang et al. |
| 8,640,958 B2 | 2/2014 | Lu et al. |
| 8,640,960 B2 | 2/2014 | Wang et al. |
| 8,643,717 B2 | 2/2014 | Li et al. |
| 8,646,692 B2 | 2/2014 | Meier et al. |
| 8,646,694 B2 | 2/2014 | Wang et al. |
| 8,657,200 B2 | 2/2014 | Ren et al. |
| 8,659,397 B2 | 2/2014 | Vargo et al. |
| 8,668,149 B2 | 3/2014 | Good |
| 8,678,285 B2 | 3/2014 | Kearney |
| 8,678,286 B2 | 3/2014 | Smith et al. |
| 8,682,077 B1 | 3/2014 | Longacre |
| D702,237 S | 4/2014 | Oberpriller et al. |
| 8,687,282 B2 | 4/2014 | Feng et al. |
| 8,692,927 B2 | 4/2014 | Pease et al. |
| 8,695,880 B2 | 4/2014 | Bremer et al. |
| 8,698,949 B2 | 4/2014 | Grunow et al. |
| 8,702,000 B2 | 4/2014 | Barber et al. |
| 8,717,494 B2 | 5/2014 | Gannon |
| 8,720,783 B2 | 5/2014 | Biss et al. |
| 8,723,804 B2 | 5/2014 | Fletcher et al. |
| 8,723,904 B2 | 5/2014 | Marty et al. |
| 8,727,223 B2 | 5/2014 | Wang |
| 8,740,082 B2 | 6/2014 | Wilz |
| 8,740,085 B2 | 6/2014 | Furlong et al. |
| 8,746,563 B2 | 6/2014 | Hennick et al. |
| 8,750,445 B2 | 6/2014 | Peake et al. |
| 8,752,766 B2 | 6/2014 | Xian et al. |
| 8,756,059 B2 | 6/2014 | Braho et al. |
| 8,757,495 B2 | 6/2014 | Qu et al. |
| 8,760,563 B2 | 6/2014 | Koziol et al. |
| 8,763,909 B2 | 7/2014 | Reed et al. |
| 8,777,108 B2 | 7/2014 | Coyle |
| 8,777,109 B2 | 7/2014 | Oberpriller et al. |
| 8,779,898 B2 | 7/2014 | Havens et al. |
| 8,781,520 B2 | 7/2014 | Payne et al. |
| 8,783,573 B2 | 7/2014 | Havens et al. |
| 8,789,757 B2 | 7/2014 | Barten |
| 8,789,758 B2 | 7/2014 | Hawley et al. |
| 8,789,759 B2 | 7/2014 | Xian et al. |
| 8,794,520 B2 | 8/2014 | Wang et al. |
| 8,794,522 B2 | 8/2014 | Ehrhart |
| 8,794,525 B2 | 8/2014 | Amundsen et al. |
| 8,794,526 B2 | 8/2014 | Wang et al. |
| 8,798,367 B2 | 8/2014 | Ellis |
| 8,807,431 B2 | 8/2014 | Wang et al. |
| 8,807,432 B2 | 8/2014 | Van Horn et al. |
| 8,820,630 B2 | 9/2014 | Qu et al. |
| 8,822,848 B2 | 9/2014 | Meagher |
| 8,824,692 B2 | 9/2014 | Sheerin et al. |
| 8,824,696 B2 | 9/2014 | Braho |
| 8,842,849 B2 | 9/2014 | Wahl et al. |
| 8,844,822 B2 | 9/2014 | Kotlarsky et al. |
| 8,844,823 B2 | 9/2014 | Fritz et al. |
| 8,849,019 B2 | 9/2014 | Li et al. |
| D716,285 S | 10/2014 | Chaney et al. |
| 8,851,383 B2 | 10/2014 | Yeakley et al. |
| 8,854,633 B2 | 10/2014 | Laffargue |
| 8,866,963 B2 | 10/2014 | Grunow et al. |
| 8,868,421 B2 | 10/2014 | Braho et al. |
| 8,868,519 B2 | 10/2014 | Maloy et al. |
| 8,868,802 B2 | 10/2014 | Barten |
| 8,868,803 B2 | 10/2014 | Caballero |
| 8,870,074 B1 | 10/2014 | Gannon |
| 8,879,639 B2 | 11/2014 | Sauerwein |
| 8,880,426 B2 | 11/2014 | Smith |
| 8,881,983 B2 | 11/2014 | Havens et al. |
| 8,881,987 B2 | 11/2014 | Wang |
| 8,903,172 B2 | 12/2014 | Smith |
| 8,908,995 B2 | 12/2014 | Benos et al. |
| 8,910,870 B2 | 12/2014 | Li et al. |
| 8,910,875 B2 | 12/2014 | Ren et al. |
| 8,914,290 B2 | 12/2014 | Hendrickson et al. |
| 8,914,788 B2 | 12/2014 | Pettinelli et al. |
| 8,915,439 B2 | 12/2014 | Feng et al. |
| 8,915,444 B2 | 12/2014 | Havens et al. |
| 8,916,789 B2 | 12/2014 | Woodburn |
| 8,918,250 B2 | 12/2014 | Hollifield |
| 8,918,564 B2 | 12/2014 | Caballero |
| 8,925,818 B2 | 1/2015 | Kosecki et al. |
| 8,939,374 B2 | 1/2015 | Jovanovski et al. |
| 8,942,480 B2 | 1/2015 | Ellis |
| 8,944,313 B2 | 2/2015 | Williams et al. |
| 8,944,327 B2 | 2/2015 | Meier et al. |
| 8,944,332 B2 | 2/2015 | Harding et al. |
| 8,950,678 B2 | 2/2015 | Germaine et al. |
| D723,560 S | 3/2015 | Zhou et al. |
| 8,967,468 B2 | 3/2015 | Gomez et al. |
| 8,971,346 B2 | 3/2015 | Sevier |
| 8,976,030 B2 | 3/2015 | Cunningham et al. |
| 8,976,368 B2 | 3/2015 | El Akel et al. |
| 8,978,981 B2 | 3/2015 | Guan |

(56) References Cited

U.S. PATENT DOCUMENTS

| | | |
|---|---|---|
| 8,978,983 B2 | 3/2015 | Bremer et al. |
| 8,978,984 B2 | 3/2015 | Hennick et al. |
| 8,985,456 B2 | 3/2015 | Zhu et al. |
| 8,985,457 B2 | 3/2015 | Soule et al. |
| 8,985,459 B2 | 3/2015 | Kearney et al. |
| 8,985,461 B2 | 3/2015 | Gelay et al. |
| 8,988,578 B2 | 3/2015 | Showering |
| 8,988,590 B2 | 3/2015 | Gillet et al. |
| 8,991,704 B2 | 3/2015 | Hopper et al. |
| 8,996,194 B2 | 3/2015 | Davis et al. |
| 8,996,384 B2 | 3/2015 | Funyak et al. |
| 8,998,091 B2 | 4/2015 | Edmonds et al. |
| 9,002,641 B2 | 4/2015 | Showering |
| 9,007,368 B2 | 4/2015 | Laffargue et al. |
| 9,010,641 B2 | 4/2015 | Qu et al. |
| 9,015,513 B2 | 4/2015 | Murawski et al. |
| 9,016,576 B2 | 4/2015 | Brady et al. |
| D730,357 S | 5/2015 | Fitch et al. |
| 9,022,288 B2 | 5/2015 | Nahill et al. |
| 9,030,964 B2 | 5/2015 | Essinger et al. |
| 9,033,240 B2 | 5/2015 | Smith et al. |
| 9,033,242 B2 | 5/2015 | Gillet et al. |
| 9,036,054 B2 | 5/2015 | Koziol et al. |
| 9,037,344 B2 | 5/2015 | Chamberlin |
| 9,038,911 B2 | 5/2015 | Xian et al. |
| 9,038,915 B2 | 5/2015 | Smith |
| D730,901 S | 6/2015 | Oberpriller et al. |
| D730,902 S | 6/2015 | Fitch et al. |
| D733,112 S | 6/2015 | Chaney et al. |
| 9,047,098 B2 | 6/2015 | Barten |
| 9,047,359 B2 | 6/2015 | Caballero et al. |
| 9,047,420 B2 | 6/2015 | Caballero |
| 9,047,525 B2 | 6/2015 | Barber |
| 9,047,531 B2 | 6/2015 | Showering et al. |
| 9,049,640 B2 | 6/2015 | Wang et al. |
| 9,053,055 B2 | 6/2015 | Caballero |
| 9,053,378 B1 | 6/2015 | Hou et al. |
| 9,053,380 B2 | 6/2015 | Xian et al. |
| 9,057,641 B2 | 6/2015 | Amundsen et al. |
| 9,058,526 B2 | 6/2015 | Powilleit |
| 9,064,165 B2 | 6/2015 | Havens et al. |
| 9,064,167 B2 | 6/2015 | Xian et al. |
| 9,064,168 B2 | 6/2015 | Todeschini et al. |
| 9,064,254 B2 | 6/2015 | Todeschini et al. |
| 9,066,032 B2 | 6/2015 | Wang |
| 9,070,032 B2 | 6/2015 | Corcoran |
| D734,339 S | 7/2015 | Zhou et al. |
| D734,751 S | 7/2015 | Oberpriller et al. |
| 9,082,023 B2 | 7/2015 | Feng et al. |
| 9,213,396 B1* | 12/2015 | Booth ................. G06F 13/4291 |
| 9,224,022 B2 | 12/2015 | Ackley et al. |
| 9,224,027 B2 | 12/2015 | Van Horn et al. |
| D747,321 S | 1/2016 | London et al. |
| 9,230,140 B1 | 1/2016 | Ackley |
| 9,250,712 B1 | 2/2016 | Todeschini |
| 9,258,033 B2 | 2/2016 | Showering |
| 9,262,633 B1 | 2/2016 | Todeschini et al. |
| 9,310,609 B2 | 4/2016 | Rueblinger et al. |
| D757,009 S | 5/2016 | Oberpriller et al. |
| 9,342,724 B2 | 5/2016 | McCloskey |
| 9,375,945 B1 | 6/2016 | Bowles |
| D760,719 S | 7/2016 | Zhou et al. |
| 9,390,596 B1 | 7/2016 | Todeschini |
| D762,604 S | 8/2016 | Fitch et al. |
| D762,647 S | 8/2016 | Fitch et al. |
| 9,412,242 B2 | 8/2016 | Van Horn et al. |
| D766,244 S | 9/2016 | Zhou et al. |
| 9,443,123 B2 | 9/2016 | Hejl |
| 9,443,222 B2 | 9/2016 | Singel et al. |
| 9,478,113 B2 | 10/2016 | Xie et al. |
| 2003/0169364 A1* | 9/2003 | Watanabe ............ G06K 9/2018 348/345 |
| 2007/0063048 A1 | 3/2007 | Havens et al. |
| 2009/0134221 A1 | 5/2009 | Zhu et al. |
| 2010/0111356 A1* | 5/2010 | Berger ................. B07C 3/14 382/101 |
| 2010/0177076 A1 | 7/2010 | Essinger et al. |
| 2010/0177080 A1 | 7/2010 | Essinger et al. |
| 2010/0177707 A1 | 7/2010 | Essinger et al. |
| 2010/0177749 A1 | 7/2010 | Essinger et al. |
| 2011/0169999 A1 | 7/2011 | Grunow et al. |
| 2011/0202554 A1 | 8/2011 | Powilleit et al. |
| 2012/0111946 A1 | 5/2012 | Golant |
| 2012/0168512 A1 | 7/2012 | Kotlarsky et al. |
| 2012/0193423 A1 | 8/2012 | Samek |
| 2012/0203647 A1 | 8/2012 | Smith |
| 2012/0223141 A1 | 9/2012 | Good et al. |
| 2013/0043312 A1 | 2/2013 | Van Horn |
| 2013/0075168 A1 | 3/2013 | Amundsen et al. |
| 2013/0175341 A1 | 7/2013 | Kearney et al. |
| 2013/0175343 A1 | 7/2013 | Good |
| 2013/0257744 A1 | 10/2013 | Daghigh et al. |
| 2013/0257759 A1 | 10/2013 | Daghigh |
| 2013/0270346 A1 | 10/2013 | Xian et al. |
| 2013/0287258 A1 | 10/2013 | Kearney |
| 2013/0292475 A1 | 11/2013 | Kotlarsky et al. |
| 2013/0292477 A1 | 11/2013 | Hennick et al. |
| 2013/0293539 A1 | 11/2013 | Hunt et al. |
| 2013/0293540 A1 | 11/2013 | Laffargue et al. |
| 2013/0306728 A1 | 11/2013 | Thuries et al. |
| 2013/0306731 A1 | 11/2013 | Pedraro |
| 2013/0307964 A1 | 11/2013 | Bremer et al. |
| 2013/0308625 A1 | 11/2013 | Park et al. |
| 2013/0313324 A1 | 11/2013 | Koziol et al. |
| 2013/0313325 A1 | 11/2013 | Wilz et al. |
| 2013/0342717 A1 | 12/2013 | Havens et al. |
| 2014/0001267 A1 | 1/2014 | Giordano et al. |
| 2014/0002828 A1 | 1/2014 | Laffargue et al. |
| 2014/0008439 A1 | 1/2014 | Wang |
| 2014/0025584 A1 | 1/2014 | Liu et al. |
| 2014/0034734 A1 | 2/2014 | Sauerwein |
| 2014/0036848 A1 | 2/2014 | Pease et al. |
| 2014/0039693 A1 | 2/2014 | Havens et al. |
| 2014/0042814 A1 | 2/2014 | Kather et al. |
| 2014/0049120 A1 | 2/2014 | Kohtz et al. |
| 2014/0049635 A1 | 2/2014 | Laffargue et al. |
| 2014/0061306 A1 | 3/2014 | Wu et al. |
| 2014/0063289 A1 | 3/2014 | Hussey et al. |
| 2014/0066136 A1 | 3/2014 | Sauerwein et al. |
| 2014/0067692 A1 | 3/2014 | Ye et al. |
| 2014/0070005 A1 | 3/2014 | Nahill et al. |
| 2014/0071840 A1 | 3/2014 | Venancio |
| 2014/0074746 A1 | 3/2014 | Wang |
| 2014/0076974 A1 | 3/2014 | Havens et al. |
| 2014/0078341 A1 | 3/2014 | Havens et al. |
| 2014/0078342 A1 | 3/2014 | Li et al. |
| 2014/0078345 A1 | 3/2014 | Showering |
| 2014/0098792 A1 | 4/2014 | Wang et al. |
| 2014/0100774 A1 | 4/2014 | Showering |
| 2014/0100813 A1 | 4/2014 | Showering |
| 2014/0103115 A1 | 4/2014 | Meier et al. |
| 2014/0104413 A1 | 4/2014 | McCloskey et al. |
| 2014/0104414 A1 | 4/2014 | McCloskey et al. |
| 2014/0104416 A1 | 4/2014 | Giordano et al. |
| 2014/0104451 A1 | 4/2014 | Todeschini et al. |
| 2014/0106594 A1 | 4/2014 | Skvoretz |
| 2014/0106725 A1 | 4/2014 | Sauerwein |
| 2014/0108010 A1 | 4/2014 | Maltseff et al. |
| 2014/0108402 A1 | 4/2014 | Gomez et al. |
| 2014/0108682 A1 | 4/2014 | Caballero |
| 2014/0110485 A1 | 4/2014 | Toa et al. |
| 2014/0114530 A1 | 4/2014 | Fitch et al. |
| 2014/0124577 A1 | 5/2014 | Wang et al. |
| 2014/0124579 A1 | 5/2014 | Ding |
| 2014/0125842 A1 | 5/2014 | Winegar |
| 2014/0125853 A1 | 5/2014 | Wang |
| 2014/0125999 A1 | 5/2014 | Longacre et al. |
| 2014/0129378 A1 | 5/2014 | Richardson |
| 2014/0131438 A1 | 5/2014 | Kearney |
| 2014/0131441 A1 | 5/2014 | Nahill et al. |
| 2014/0131443 A1 | 5/2014 | Smith |
| 2014/0131444 A1 | 5/2014 | Wang |
| 2014/0131445 A1 | 5/2014 | Ding et al. |

(56) References Cited

U.S. PATENT DOCUMENTS

| | | |
|---|---|---|
| 2014/0131448 A1 | 5/2014 | Xian et al. |
| 2014/0133379 A1 | 5/2014 | Wang et al. |
| 2014/0136208 A1 | 5/2014 | Maltseff et al. |
| 2014/0140585 A1 | 5/2014 | Wang |
| 2014/0151453 A1 | 6/2014 | Meier et al. |
| 2014/0152882 A1 | 6/2014 | Samek et al. |
| 2014/0158770 A1 | 6/2014 | Sevier et al. |
| 2014/0159869 A1 | 6/2014 | Zumsteg et al. |
| 2014/0166755 A1 | 6/2014 | Liu et al. |
| 2014/0166757 A1 | 6/2014 | Smith |
| 2014/0166759 A1 | 6/2014 | Liu et al. |
| 2014/0168787 A1 | 6/2014 | Wang et al. |
| 2014/0175165 A1 | 6/2014 | Havens et al. |
| 2014/0175172 A1 | 6/2014 | Jovanovski et al. |
| 2014/0191644 A1 | 7/2014 | Chaney |
| 2014/0191913 A1 | 7/2014 | Ge et al. |
| 2014/0197238 A1 | 7/2014 | Liu et al. |
| 2014/0197239 A1 | 7/2014 | Havens et al. |
| 2014/0197304 A1 | 7/2014 | Feng et al. |
| 2014/0203087 A1 | 7/2014 | Smith et al. |
| 2014/0204268 A1 | 7/2014 | Grunow et al. |
| 2014/0214631 A1 | 7/2014 | Hansen |
| 2014/0217166 A1 | 8/2014 | Berthiaume et al. |
| 2014/0217180 A1 | 8/2014 | Liu |
| 2014/0231500 A1 | 8/2014 | Ehrhart et al. |
| 2014/0232930 A1 | 8/2014 | Anderson |
| 2014/0247315 A1 | 9/2014 | Marty et al. |
| 2014/0263493 A1 | 9/2014 | Amurgis et al. |
| 2014/0263645 A1 | 9/2014 | Smith et al. |
| 2014/0270196 A1 | 9/2014 | Braho et al. |
| 2014/0270229 A1 | 9/2014 | Braho |
| 2014/0278387 A1 | 9/2014 | DiGregorio |
| 2014/0282210 A1 | 9/2014 | Bianconi |
| 2014/0284384 A1 | 9/2014 | Lu et al. |
| 2014/0288933 A1 | 9/2014 | Braho et al. |
| 2014/0297058 A1 | 10/2014 | Barker et al. |
| 2014/0299665 A1 | 10/2014 | Barber et al. |
| 2014/0312121 A1 | 10/2014 | Lu et al. |
| 2014/0319220 A1 | 10/2014 | Coyle |
| 2014/0319221 A1 | 10/2014 | Oberpriller et al. |
| 2014/0326787 A1 | 11/2014 | Barten |
| 2014/0332590 A1 | 11/2014 | Wang et al. |
| 2014/0344943 A1 | 11/2014 | Todeschini et al. |
| 2014/0346233 A1 | 11/2014 | Liu et al. |
| 2014/0351317 A1 | 11/2014 | Smith et al. |
| 2014/0353373 A1 | 12/2014 | Van Horn et al. |
| 2014/0361073 A1 | 12/2014 | Qu et al. |
| 2014/0361082 A1 | 12/2014 | Xian et al. |
| 2014/0362184 A1 | 12/2014 | Jovanovski et al. |
| 2014/0363015 A1 | 12/2014 | Braho |
| 2014/0369511 A1 | 12/2014 | Sheerin et al. |
| 2014/0374483 A1 | 12/2014 | Lu |
| 2014/0374485 A1 | 12/2014 | Xian et al. |
| 2015/0001301 A1 | 1/2015 | Ouyang |
| 2015/0001304 A1 | 1/2015 | Todeschini |
| 2015/0003673 A1 | 1/2015 | Fletcher |
| 2015/0009338 A1 | 1/2015 | Laffargue et al. |
| 2015/0009610 A1 | 1/2015 | London et al. |
| 2015/0014416 A1 | 1/2015 | Kotlarsky et al. |
| 2015/0021397 A1 | 1/2015 | Rueblinger et al. |
| 2015/0028102 A1 | 1/2015 | Ren et al. |
| 2015/0028103 A1 | 1/2015 | Jiang |
| 2015/0028104 A1 | 1/2015 | Ma et al. |
| 2015/0029002 A1 | 1/2015 | Yeakley et al. |
| 2015/0032709 A1 | 1/2015 | Maloy et al. |
| 2015/0039309 A1 | 2/2015 | Braho et al. |
| 2015/0040378 A1 | 2/2015 | Saber et al. |
| 2015/0048168 A1 | 2/2015 | Fritz et al. |
| 2015/0049347 A1 | 2/2015 | Laffargue et al. |
| 2015/0051992 A1 | 2/2015 | Smith |
| 2015/0053766 A1 | 2/2015 | Havens et al. |
| 2015/0053768 A1 | 2/2015 | Wang et al. |
| 2015/0053769 A1 | 2/2015 | Thuries et al. |
| 2015/0062366 A1 | 3/2015 | Liu et al. |
| 2015/0063215 A1 | 3/2015 | Wang |
| 2015/0063676 A1 | 3/2015 | Lloyd et al. |
| 2015/0069130 A1 | 3/2015 | Gannon |
| 2015/0071819 A1 | 3/2015 | Todeschini |
| 2015/0083800 A1 | 3/2015 | Li et al. |
| 2015/0086114 A1 | 3/2015 | Todeschini |
| 2015/0088522 A1 | 3/2015 | Hendrickson et al. |
| 2015/0096872 A1 | 4/2015 | Woodburn |
| 2015/0099557 A1 | 4/2015 | Pettinelli et al. |
| 2015/0100196 A1 | 4/2015 | Hollifield |
| 2015/0102109 A1 | 4/2015 | Huck |
| 2015/0115035 A1 | 4/2015 | Meier et al. |
| 2015/0127791 A1 | 5/2015 | Kosecki et al. |
| 2015/0128116 A1 | 5/2015 | Chen et al. |
| 2015/0129659 A1 | 5/2015 | Feng et al. |
| 2015/0133047 A1 | 5/2015 | Smith et al. |
| 2015/0134470 A1 | 5/2015 | Hejl et al. |
| 2015/0136851 A1 | 5/2015 | Harding et al. |
| 2015/0136854 A1 | 5/2015 | Lu et al. |
| 2015/0142492 A1 | 5/2015 | Kumar |
| 2015/0144692 A1 | 5/2015 | Hejl |
| 2015/0144698 A1 | 5/2015 | Teng et al. |
| 2015/0144701 A1 | 5/2015 | Xian et al. |
| 2015/0149946 A1 | 5/2015 | Benos et al. |
| 2015/0161429 A1 | 6/2015 | Xian |
| 2015/0169925 A1 | 6/2015 | Chen et al. |
| 2015/0169929 A1 | 6/2015 | Williams et al. |
| 2015/0186703 A1 | 7/2015 | Chen et al. |
| 2015/0193644 A1 | 7/2015 | Kearney et al. |
| 2015/0193645 A1 | 7/2015 | Colavito et al. |
| 2015/0199957 A1 | 7/2015 | Funyak et al. |
| 2015/0204671 A1 | 7/2015 | Showering |
| 2015/0210199 A1 | 7/2015 | Payne |
| 2015/0220753 A1 | 8/2015 | Zhu et al. |
| 2015/0254485 A1 | 9/2015 | Feng et al. |
| 2015/0327012 A1 | 11/2015 | Bian et al. |
| 2016/0014251 A1 | 1/2016 | Hejl |
| 2016/0040982 A1 | 2/2016 | Li et al. |
| 2016/0042241 A1 | 2/2016 | Todeschini |
| 2016/0057230 A1 | 2/2016 | Todeschini et al. |
| 2016/0109219 A1 | 4/2016 | Ackley et al. |
| 2016/0109220 A1 | 4/2016 | Laffargue |
| 2016/0109224 A1 | 4/2016 | Thuries et al. |
| 2016/0112631 A1 | 4/2016 | Ackley et al. |
| 2016/0112643 A1 | 4/2016 | Laffargue et al. |
| 2016/0124516 A1 | 5/2016 | Schoon et al. |
| 2016/0125217 A1 | 5/2016 | Todeschini |
| 2016/0125342 A1 | 5/2016 | Miller et al. |
| 2016/0125873 A1 | 5/2016 | Braho et al. |
| 2016/0133253 A1 | 5/2016 | Braho et al. |
| 2016/0171720 A1 | 6/2016 | Todeschini |
| 2016/0178479 A1 | 6/2016 | Goldsmith |
| 2016/0180678 A1 | 6/2016 | Ackley et al. |
| 2016/0189087 A1 | 6/2016 | Morton et al. |
| 2016/0227912 A1 | 8/2016 | Oberpriller et al. |
| 2016/0232891 A1 | 8/2016 | Pecorari |
| 2016/0292477 A1 | 10/2016 | Bidwell |
| 2016/0294779 A1 | 10/2016 | Yeakley et al. |
| 2016/0306769 A1 | 10/2016 | Kohtz et al. |
| 2016/0314276 A1 | 10/2016 | Wilz, Sr. et al. |
| 2016/0314294 A1 | 10/2016 | Kubler et al. |

FOREIGN PATENT DOCUMENTS

| | | |
|---|---|---|
| WO | 2014019130 A1 | 2/2014 |
| WO | 2014110495 A1 | 7/2014 |

OTHER PUBLICATIONS

U.S. Appl. No. 29/525,068 for Tablet Computer With Removable Scanning Device filed Apr. 27, 2015 (Schulte et al.); 19 pages.

U.S. Appl. No. 29/468,118 for an Electronic Device Case, filed Sep. 26, 2013 (Oberpriller et al.); 44 pages.

U.S. Appl. No. 29/530,600 for CYCLONE filed Jun. 18, 2015 (Vargo et al); 16 pages.

U.S. Appl. No. 14/707,123 for Application Independent DEX/UCS Interface filed May 8, 2015 (Pape); 47 pages.

U.S. Appl. No. 14/283,282 for Terminal Having Illumination and (56) References Cited

OTHER PUBLICATIONS

Focus Control filed May 21, 2014 (Liu et al.); 31 pages; now abandoned.
U.S. Appl. No. 14/705,407 for Method and System to Protect Software-Based Network-Connected Devices From Advanced Persistent Threat filed May 6, 2015 (Hussey et al.); 42 pages.
U.S. Appl. No. 14/704,050 for Intermediate Linear Positioning filed May 5, 2015 (Charpentier et al); 60 pages.
U.S. Appl. No. 14/705,012 for Hands-Free Human Interface Responsive to a Driver of a Vehicle filed May 6, 2015(Fitch et al.); 44 pages.
U.S. Appl. No. 14/715,672 for Augumented Reality Enabled Hazard Display filed May 19, 2015 (Venkatesha et al.); 35 pages.
U.S. Appl. No. 14/735,717 for Indicia-Reading Systems Having an Interface With a User'S Nervous System filed Jun. 10, 2015 (Todeschini); 39 pages.
U.S. Appl. No. 14/702,110 for System and Method for Regulating Barcode Data Injection Into a Running Application on a Smart Device filed May 1, 2015 (Todeschini et al.); 38 pages.
U.S. Appl. No. 14/747,197 for Optical Pattern Projector filed Jun. 23, 2015 (Thuries et al.); 33 pages.
U.S. Appl. No. 14/702,979 for Tracking Battery Conditions filed May 4, 2015 (Young et al.); 70 pages.
U.S. Appl. No. 29/529,441 for Indicia Reading Device filed Jun. 8, 2015 (Zhou et al.); 14 pages.
U.S. Appl. No. 14/747,490 for Dual-Projector Three-Dimensional Scanner filed Jun. 23, 2015 (Jovanovski et al.); 40 pages.
U.S. Appl. No. 14/740,320 for Tactile Switch Fora Mobile Electronic Device filed Jun. 16, 2015 (Barndringa); 38 pages.
U.S. Appl. No. 14/740,373 for Calibrating a Volume Dimensioner filed Jun. 16, 2015 (Ackley et al.); 63 pages.
Intersil, ISL29125 "Digital Red, Green and Blue color Light Sensor with IR Blocking Filter" dated Jan. 24, 2014, 17 pages.
Intersil, ISL29120 "Digital Output, Low Power, Red, Green, and Blue color Light Sensor" dated May 29, 2012, 8 pages.
The Label Experts, "Label Lingo-Label Sensing", http://barcode-labels.com/technical-support/label-lingo-label-sensing/, dated Apr. 15, 2016, 2 pages.
Intermec, "EasyCoder 201 II Black Mark Sensor Kit: Installation Instructions," dated Sep. 1998, 7 pages.
Honeywell Sensing and Productivity Solutions, "Honeywell Thermal Printers & Media Supplies; Product Brochure" ; Dated 2016, 8 pages.
U.S. Appl. No. 13/367,978, filed Feb. 7, 2012, (Feng et al.); now abandoned.
U.S. Appl. No. 14/277,337 for Multipurpose Optical Reader, filed May 14, 2014 (Jovanovski et 31); 59 pages; now abandoned.
U.S. Appl. No. 14/446,391 for Multifunction Point of Sale Apparatus With Optical Signature Capture filed Jul. 30, 2014 (Good et al.); 37 pages; now abandoned.
U.S. Appl. No. 29/516,892 for Table Computer filed Feb. 6, 2015 (Bidwell et al.); 13 pages.
U.S. Appl. No. 29/523,098 for Handle for a Tablet Computer filed Apr. 7, 2015 (Bidwell et al.); 17 pages.
U.S. Appl. No. 29/528,890 for Mobile Computer Housing filed Jun. 2, 2015 (Fitch et al.); 61 pages.
U.S. Appl. No. 29/526,918 for Charging Base filed May 14, 2015 (Fitch et al.); 10 pages.

* cited by examiner

PRINTER METHOD AND APPARATUS

FIELD OF THE INVENTION

The present invention relates to printing devices and in particular to portable printing devices such as those used for printing labels and the like.

BACKGROUND

Pre-printed (forms, etc.) or fixed size (labels, etc.) thermal media should be correctly aligned within a printer in order for the printing to properly register onto the media. The most common method to insure accurate media alignment is use of a pre-printed "black mark" on the back or the front side of the media.

Unfortunately, a front printed black mark may result in a large inter-form/label gap or may introduce an undesired element (a black mark) to a print canvas. The back printed mark also adds complexity to a printer design, since it requires installation of a reflective photoelectric sensor on the back side of the printer door. Infrared light transmitters are traditionally used for this purpose. However, traditional infrared reflective photoelectric sensors are sensitive to direct sunlight and often fail when used in a peel-and-present printing mechanism. This arrangement is also limited to only sensing a level of transmitted infrared light reflection from an object and suffers from wide variations in received signal strength due to quality and variations in the material of the sensor and its potentially imprecise placement during assembly. More often than not costly sensor sorting and matching operations have to be implemented to alleviate sensitivity error.

Therefore, a need exists for a better mechanism to detect proper alignment of forms in a printer.

SUMMARY

Accordingly, in one aspect, the present invention embraces a printer for printing on a print medium having preprinted elements that make up a form. A light source directs light toward a print medium path. A red-green-blue (RGB) light sensor is positioned to receive light from the light source that is reflected by the print medium. An infrared light filter is situated between the RGB light sensor and the paper so as to filter out infrared light entering the RGB light sensor. The RGB light sensor has an output coupled to a programmed processor. The programmed processor is programmed to detect at least one form element in the output from the RGB light sensor. In certain example embodiments, the programmed processor is further programmed to: retrieve a stored electronic representation of the form; match the form elements to the stored electronic representation of the form to identify locations on the form; and control printing to the form.

In certain example embodiments, an I2C interface is situated between the RGB sensor and the processor. In certain example embodiments, the form elements comprise at least one cell designated for bounding data to be printed. In certain example embodiments, the processor is further programmed to: advance the print medium through the printer; identify form elements in the output from the RGB light sensor as the print medium is being advanced through the printer; and store the identified form elements to memory as an electronic representation of the form. In certain example embodiments, the processor is further programmed to detect light intensity, and the processor determines that the printer is out of media by detecting light intensity below a specified threshold In certain example embodiments, the processor is further programmed to detect light intensity and the processor determines that the printer contains print media by detecting light intensity greater than a specified threshold. In certain example embodiments, the processor stores a dot count representing a number of lines of the print media as a measure of location along the form where a form element is situated.

In another example embodiment, a printer for printing on a print medium having preprinted elements that make up a form has a light source that directs light toward a print medium path. A red-green-blue (RGB) light sensor is positioned to receive light from the light source that is reflected by the print medium. An infrared light filter is situated between the RGB light sensor and the paper so as to filter out infrared light entering the RGB light sensor. A programmed processor is provided. The RGB light sensor has an output coupled to the programmed processor. The programmed processor is programmed to: advance the print medium through the printer; identify form elements in the output from the RGB light sensor as the print medium is being advanced through the printer; and store the identified form elements to memory as an electronic representation of the form; detect at least one form element in the output from the RGB light sensor; retrieve a stored electronic representation of the form; match the form elements to the stored electronic representation of the form to identify locations on the form, where the form elements comprise at least one cell designated for bounding data to be printed; and control printing to the form.

In certain example embodiments, an I2C interface is situated between the RGB sensor and the processor. In certain example embodiments, the processor is further programmed to detect light intensity, and the processor determines that the printer is out of media by detecting light intensity below a specified threshold. In certain example embodiments, the processor is further programmed to detect light intensity and where the processor determines that the printer contains print media by detecting light intensity greater than a specified threshold. In certain example embodiments, the processor stores a dot count representing a number of lines of the print media as a measure of location along the form where a form element is situated.

In yet another example embodiment, a method of printing on a print medium having preprinted elements that make up a form, involves: at a programmed processor, receiving an output signal from a red-green-blue (RGB) light sensor; advancing the print medium through the printer; detecting at least one form element in the output from the RGB light sensor as the print medium is advanced through the printer; retrieving a stored electronic representation of the form; matching the form elements to the stored electronic representation of the form to identify locations on the form; and printing to the form.

In certain example embodiments, the method further involves filtering infrared light out of light that is passed to the RGB light sensor. In certain example embodiments, the output signal from the RGB sensor is passed to the processor using an I2C interface. In certain example embodiments, the form elements comprise at least one cell designated for bounding data to be printed. In certain example embodiments, an initialization involves: advancing the print medium through the printer; identifying form elements in the output from the RGB light sensor as the print medium is being advanced through the printer; and storing the identified form elements to memory as an electronic representation of the form. In certain example embodiments, the process further involves detecting light intensity and determining that the printer is out of media by detecting light intensity below a specified threshold. In certain example embodiments, the method further involves detecting light intensity and determining the printer contains print media by detecting light intensity greater than a specified threshold. In certain example embodiments, the method further involves storing a dot count representing a number of lines of the print media as a measure of location along the form where a form element is situated.

The foregoing illustrative summary, as well as other exemplary objectives and/or advantages of the invention, and the manner in which the same are accomplished, are further explained within the following detailed description and its accompanying drawings.

DETAILED DESCRIPTION

The present invention embraces a printer mechanism and method of calibration and operation thereof.

In accord with the present teachings, a red-green-blue (RGB) color light sensor can be used to detect pre-printed elements on the front side of the thermal media and to perform required media alignment for various forms and labels (e.g., bar code labels and parking violation citations). This eliminates any need for a black mark or/and back side reflective photo sensor. The RGB color light sensor can be used in conjunction with an infrared (IR) blocking filter to avoid sensing errors caused by direct sunlight and other infrared sources.

In accord with certain example embodiments, instead of using an infrared reflective sensor in the print head mechanism, an RGB color light sensors is utilized. For example: Intersil part number ISL29120 can be used. In another example, a peel-and-present mechanism can utilize an RGB color light sensor with IR blocking filter such as for example Intersil part number ISL29125.

As previously noted, some label printers may utilize have a "reflective" sensor that relies on black lines or marks printed on the back of the label liner. The black mark tells the printer how the label is registered. But by utilizing the RGB sensor, an image of the label can be stored and used by the printer to achieve proper alignment without use of such a black mark. Since the black mark has height, width and position requirements that have to be considered in advance by the thermal paper manufacturer. It occupies space that could have been otherwise used for printing user data. The RGB sensor as taught herein can be used eliminate need for a back side mark and therefore a back side IR sensor.

Figure 1:
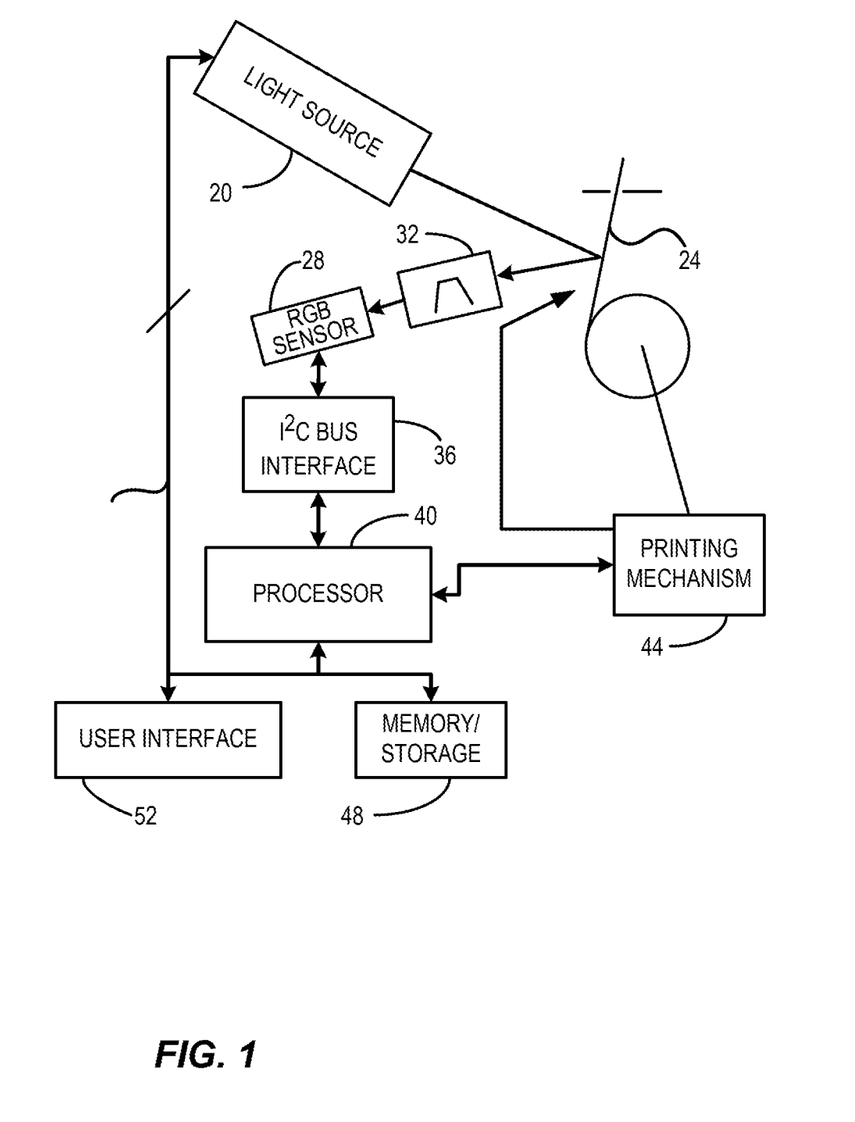
FIG. 1 depicts an example printer mechanism consistent with certain example implementations.

Referring now to FIG. 1, a printing mechanism consistent with certain illustrative embodiments is depicted. In such an embodiment, a visible light source 20 (e.g., a wide spectrum visible light LED arrangement) is used to illuminate the top surface of a print medium (e.g., a rolled print medium) 24. The visible light reflected from the print medium 24 is detected by RGB sensor 28. In order to minimize noise from infrared light, an infrared filter 32 is used to block or highly attenuate the IR spectrum from the RGB sensor 28. The output of the RGB sensor is passed via a suitable bus (e.g., an I2C bus interface) interface 36 to a processor 40.

Processor 40 controls and oversees operation of the printer including control of the print queue and instructions to the printing mechanism 44 to control operations such as advancing the print medium and burning or otherwise printing to the medium. Processor 40 may also control operation of light source 20 and RGB sensor 28 utilizing instructions stored in memory or other storage 48. Memory or other storage 48 is also utilized to store information representing one or more forms that may be used in the printer. The user interacts with the printer via any suitable user interface 52.

Figure 2:
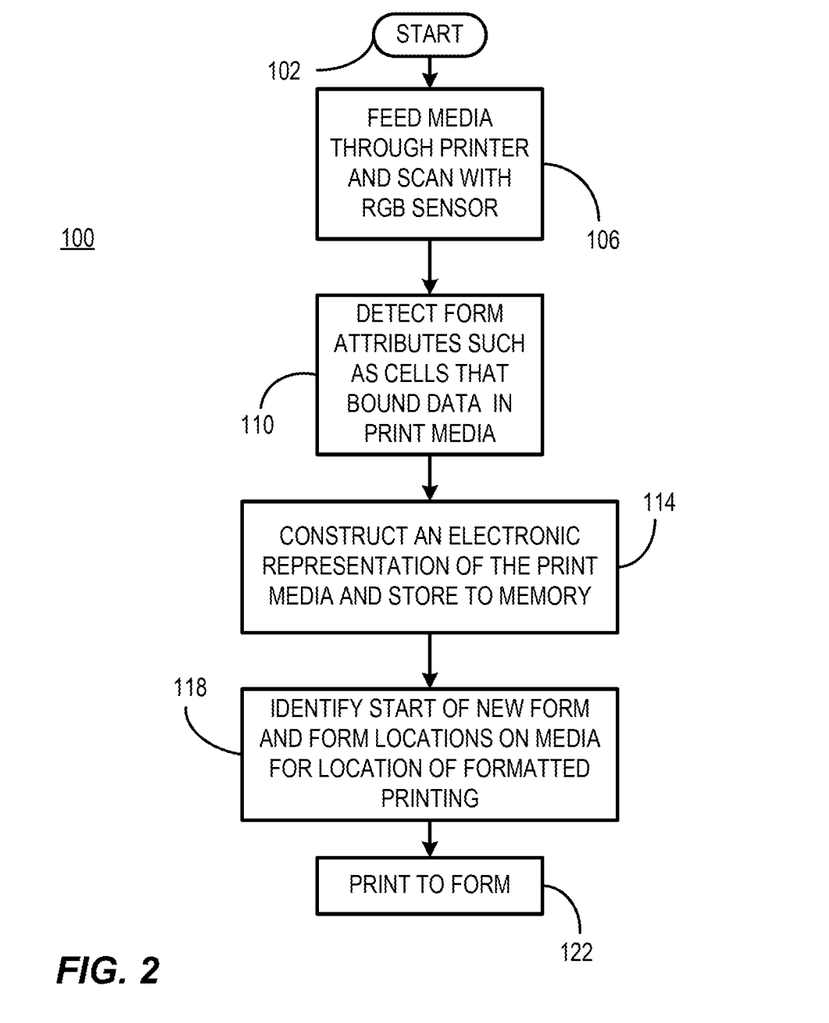
FIG. 2 is an example of a flow chart an overall process used by an example printer consistent with certain example implementations.

FIG. 2 represents an example high level flow chart 100 of an example process for use by a printing mechanism such as is discussed herein in a manner consistent with certain embodiments of the present invention. The overall process starts at 102 after which a length of media such as a pre-printed form is fed through the printer at 106. While the media is being fed through the printer, the RGB sensor detects at least one form element in the output from the RGB light sensor. Such form elements, for example, might include cells with lines around them that are intended to serve as boundaries to contain certain information. For example, in the case of many forms including parking citations there may be a cell that is designated as a boundary for printing of the date. Hence, the location of the cells and other form elements (e.g., lines or other printed attributes) can be used to characterize the form and to identify the beginning of the form. So, at 110, the processor can analyze the output of the RGB sensor to detect cells and other form elements in the RGB sensor output so as to characterize the form and the data cells of the form.

As the form is passed through the printer, the output from the RGB sensor can be used to essentially construct an electronic representation of the print media at 114 and store it to memory so that the stored electronic representation of the form can be retrieved from memory to aid in identifying the beginning of the form and assure that the data being printed to the form is printed in the correct location. The processor matches the form elements to the stored electronic representation of the form to identify a beginning of the form at 118 and from there can control printing to the form of the print media at 122.

Figure 3:
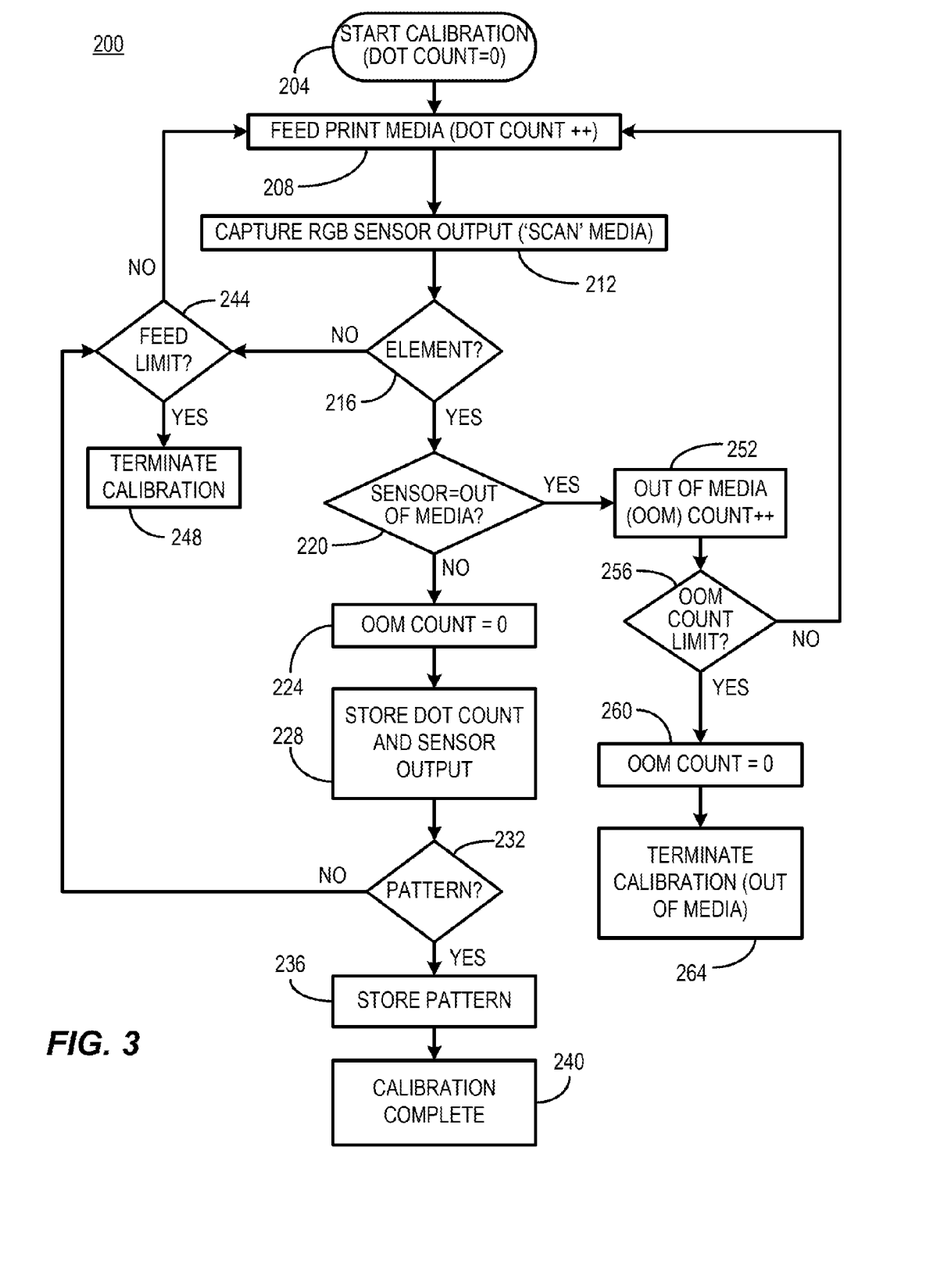
FIG. 3 is an example of a flow chart of a calibration process consistent with certain example embodiments.

Turning now to FIG. 3, a calibration process for calibrating the printer to a new form is depicted in process 200 starting at 204 where a dot count is initialized to 0. The dot count represents a count of the number of lines of dots as a measure of distance down the form. At 208, the print medium is fed through the printer and the dot count is incremented as the medium is fed through so as to keep track of how far down the form the medium has been advanced. As the print medium is fed through, the RGB sensor reads the visible light reflected from the print medium and passes data representing the sensor output to the processor. During this process, the processor is monitoring the data from the RGB sensor in an attempt to discover a form element such as a form's data cell(s) in the images captured by the RGB sensor. The dot count is incremented by one for every advance of the print medium through the printer. Each form element identified and its location as measured in dot count is stored.

The RGB sensor data as processed by the processor can easily detect an end of plain white or light colored media at 220 if encountered by, for example simply measuring the light intensity that is detected. If the media (e.g., thermal printing paper) passes over a dark colored background such as a roller at the location of imaging, a low light intensity can be interpreted as "out-of-media" (OOM) whereas a higher light intensity is interpreted as "media present." In this manner, a high to low lux transition corresponds to an "out-of-media" event as paper is passing through the printer. Similarly, a low to high lux transition corresponds to a "media in/media door closed" event. In carrying out this detection of OOM, the light intensity from the detector can be compared to a threshold (e.g., 5-15% of the maximum output of the sensor) to determine if an OOM event is occurring. So, if the light intensity drops below, for example, 10% of the RGB sensor's maximum output, the processor can deduce that the printer is out of paper and generate a suitable alert.

For "peel and present" media, light intensity readings can also be used, for example, a low lux reading can be interpreted as "no label" and a higher lux reading can be interpreted as a "label present".

If the OOM event has not occurred at 220, then the OOM count equals zero at 224 and the process proceeds to 228 where a dot count and sensor output is stored. The dot count represents a vertical location on the form. The sensor output is analyzed by the processor at 232 to determine if a pattern has been detected. A pre-printed pattern is a collection of matching RGB sensor readings with repeating dot line spacings (vertically and horizontally). If a repeating pattern is detected at 232, that pattern represents at least a portion of the form's pattern which can then be stored to the memory or other storage at 236 and the calibration process is complete at 240.

An element at 216 can be detected by, for example, detecting a light intensity corresponding to out of media, a black mark (aka, Q-mark), pre-printed text, table, drawing, cell, line, etc. When an element is discovered at 216, the element can be checked to see if the element matches a light intensity corresponding to an out-of-media value at 220. If it does, the OOM count is incremented at 252. In order to assure that the printer is really out of media and is not being tricked by a print media defect, several (e.g., 5-10) consecutive OOM detections are used as a limit at 256.

If, at 216, an element is not discovered the process passes to 244 where a maximum number N of consecutive blank or empty values have been encountered. If the limit N has been reached, then the calibration is terminated at 248 with an error so as to prevent plane white paper from being advanced to the end of the media roll. Until the feed limit is reached, the process advances the print medium through the printer one dot line at a time at 208.

If the RGB sensor produces a signal indicative that the end of the medium has been reached at 220, the process goes to 252 as previously discussed where the OOM count is incremented by one dot line. Control then passes to 256 to determine if the OOM count has exceeded an OOM count limit M. If not, control passes back to 208 and the process continues. If the OOM count limit M is reached at 256, the OOM count is initialized to zero at 260 and the calibration is terminated at 264 in view of the printer being apparently out of print media.

Figure 4:
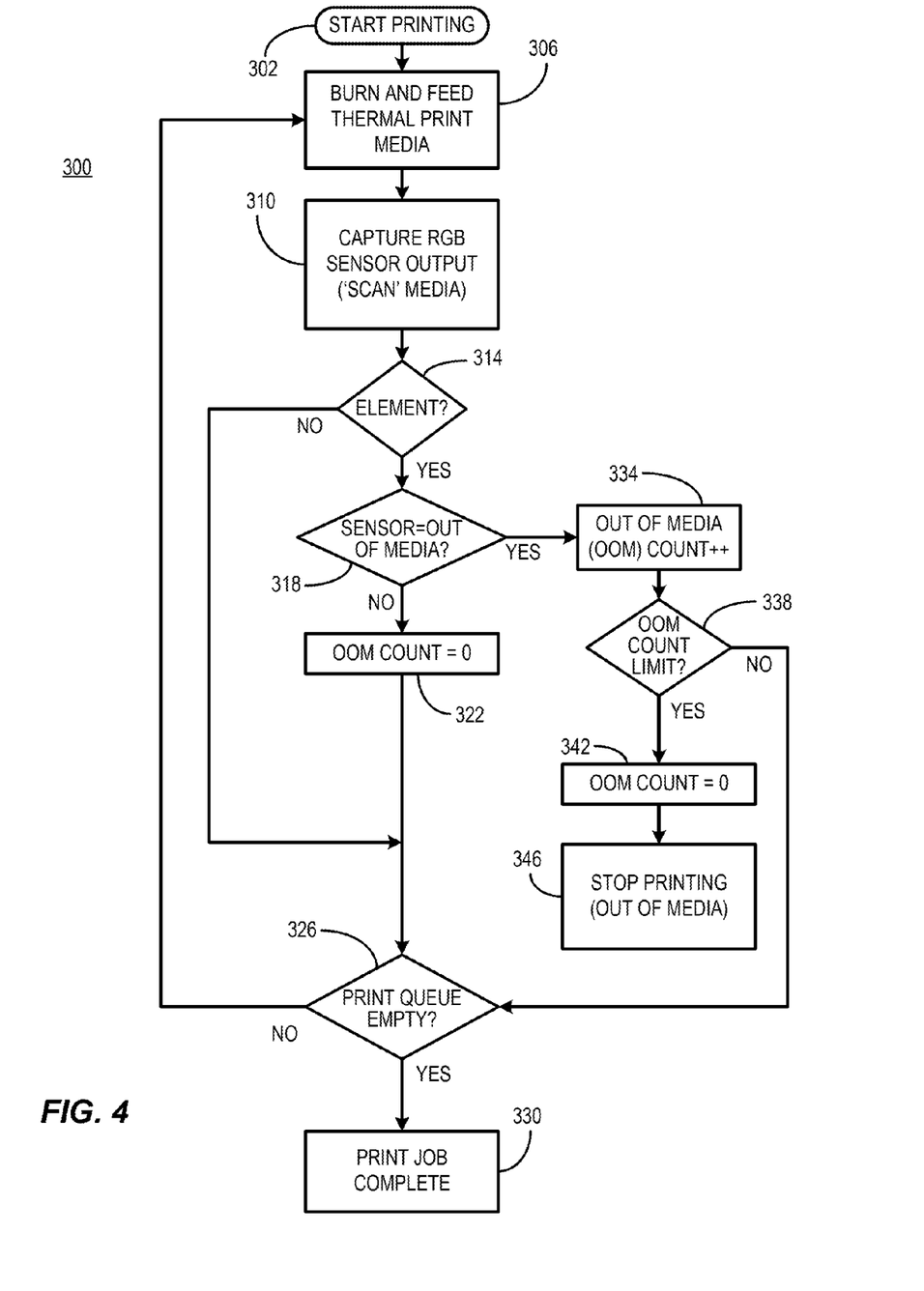
FIG. 4 is an example of a flow chart depicting a printing process consistent with certain example embodiments.

Referring now to FIG. 4, an example printing process is depicted in flow chart 300 starting at 302. At 306, the print medium (e.g., thermal printer paper) is fed and burned for a dot line. The RGB sensor outputs a signal to the processor at 310 and at 314, the process determines if an element has been encountered in the same manner previously described. If so, control passes to 318. If not the process proceeds to 326 to determine if the print queue is empty.

At 318, if the sensor is not generating an OOM signal, the OOM count is set to zero at 322 and control passes to 326. If the print queue is empty at 326, the print job is deemed complete at 330 and the print process ends. If the print queue is not empty at 326, control passes back to 306 where the next dot line is incremented and burned.

If an out of media sensor reading is obtained at 318, then the OOM count is incremented at 334 (again, this is to assure that enough consecutive OOM counts are received to assure that the end of the media has been reached). If the OOM count limit is reached at 338, the OOM count is reset to zero at 342 and the printer stops printing at 346. The printer may generate an alert to advise the user that the printer is out of media.

Figure 5:
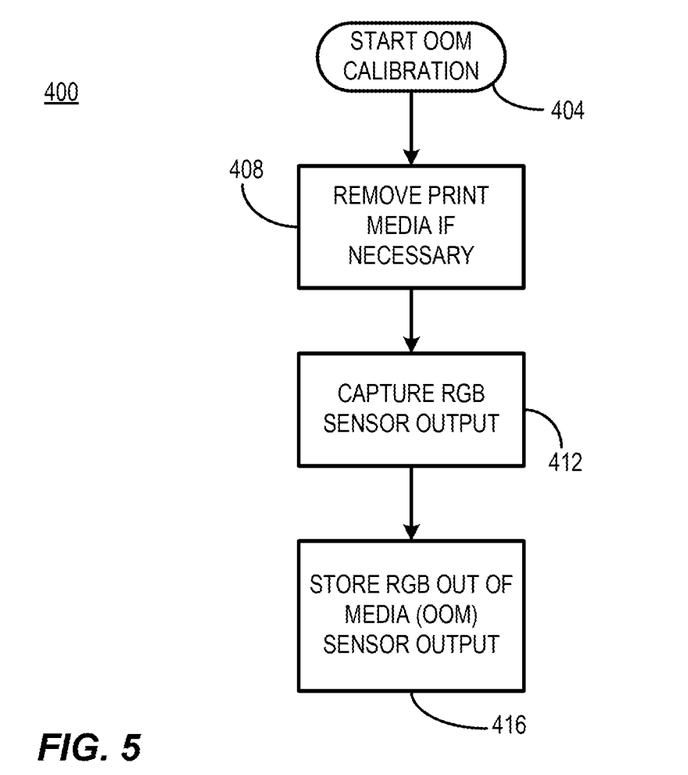
FIG. 5 is an example of a calibration process for ascertaining an appropriate RGB sensor output value representing an out of media condition.

The out of media sensor reading may be calibrated by the process depicted in the example flow chart 400 of FIG. 5 starting at 404. At 408 print media, if any, is removed from the printer and the RBG sensor output is captured at 412. This sensor output represents an OOM signal level for no media present. This can be stored as the OOM sensor output at 416. Since this value can vary somewhat, the process may set a threshold near this value that is used as the threshold beyond which an OOM signal is deemed to have occurred.

Using an RGB sensor in the print mechanism can open up a wide variety of processing options that can prove useful in carrying out the printing function. The RGB sensor can use both reflective and transmissive sensing methods for plain media detection. The RGB sensor can also be configured to trigger an interrupt upon detection of a particular color and this can be used for various control functions. When a printer utilizes a back side sensor, the printer arrangement generally includes a flex cable that is routed through a paper door hinge, but this is not necessary when the printer only utilizes a front side RGB sensor.

Thus, as described above, a printer has a light source that directs light toward a location for print medium. An RGB sensor is positioned to receive light from the light source that is reflected by the print medium. An infrared light filter is situated between the RGB sensor and the paper to filter out infrared light. A programmed processor is coupled to an output of the RGB sensor in order to detect form elements in the output from the RGB light sensor, retrieve a stored electronic representation of a form, match the form elements to the stored electronic representation of the form to identify locations on the form, and control printing to the form.

To supplement the present disclosure, this application incorporates entirely by reference the following commonly assigned patents, patent application publications, and patent applications:

U.S. Pat. No. 6,832,725; U.S. Pat. No. 7,128,266;
U.S. Pat. No. 7,159,783; U.S. Pat. No. 7,413,127;
U.S. Pat. No. 7,726,575; U.S. Pat. No. 8,294,969;
U.S. Pat. No. 8,317,105; U.S. Pat. No. 8,322,622;
U.S. Pat. No. 8,366,005; U.S. Pat. No. 8,371,507;
U.S. Pat. No. 8,376,233; U.S. Pat. No. 8,381,979;
U.S. Pat. No. 8,390,909; U.S. Pat. No. 8,408,464;
U.S. Pat. No. 8,408,468; U.S. Pat. No. 8,408,469;
U.S. Pat. No. 8,424,768; U.S. Pat. No. 8,448,863;
U.S. Pat. No. 8,457,013; U.S. Pat. No. 8,459,557;

U.S. Pat. No. 8,469,272; U.S. Pat. No. 8,474,712;
U.S. Pat. No. 8,479,992; U.S. Pat. No. 8,490,877;
U.S. Pat. No. 8,517,271; U.S. Pat. No. 8,523,076;
U.S. Pat. No. 8,528,818; U.S. Pat. No. 8,544,737;
U.S. Pat. No. 8,548,242; U.S. Pat. No. 8,548,420;
U.S. Pat. No. 8,550,335; U.S. Pat. No. 8,550,354;
U.S. Pat. No. 8,550,357; U.S. Pat. No. 8,556,174;
U.S. Pat. No. 8,556,176; U.S. Pat. No. 8,556,177;
U.S. Pat. No. 8,559,767; U.S. Pat. No. 8,599,957;
U.S. Pat. No. 8,561,895; U.S. Pat. No. 8,561,903;
U.S. Pat. No. 8,561,905; U.S. Pat. No. 8,565,107;
U.S. Pat. No. 8,571,307; U.S. Pat. No. 8,579,200;
U.S. Pat. No. 8,583,924; U.S. Pat. No. 8,584,945;
U.S. Pat. No. 8,587,595; U.S. Pat. No. 8,587,697;
U.S. Pat. No. 8,588,869; U.S. Pat. No. 8,590,789;
U.S. Pat. No. 8,596,539; U.S. Pat. No. 8,596,542;
U.S. Pat. No. 8,596,543; U.S. Pat. No. 8,599,271;
U.S. Pat. No. 8,599,957; U.S. Pat. No. 8,600,158;
U.S. Pat. No. 8,600,167; U.S. Pat. No. 8,602,309;
U.S. Pat. No. 8,608,053; U.S. Pat. No. 8,608,071;
U.S. Pat. No. 8,611,309; U.S. Pat. No. 8,615,487;
U.S. Pat. No. 8,616,454; U.S. Pat. No. 8,621,123;
U.S. Pat. No. 8,622,303; U.S. Pat. No. 8,628,013;
U.S. Pat. No. 8,628,015; U.S. Pat. No. 8,628,016;
U.S. Pat. No. 8,629,926; U.S. Pat. No. 8,630,491;
U.S. Pat. No. 8,635,309; U.S. Pat. No. 8,636,200;
U.S. Pat. No. 8,636,212; U.S. Pat. No. 8,636,215;
U.S. Pat. No. 8,636,224; U.S. Pat. No. 8,638,806;
U.S. Pat. No. 8,640,958; U.S. Pat. No. 8,640,960;
U.S. Pat. No. 8,643,717; U.S. Pat. No. 8,646,692;
U.S. Pat. No. 8,646,694; U.S. Pat. No. 8,657,200;
U.S. Pat. No. 8,659,397; U.S. Pat. No. 8,668,149;
U.S. Pat. No. 8,678,285; U.S. Pat. No. 8,678,286;
U.S. Pat. No. 8,682,077; U.S. Pat. No. 8,687,282;
U.S. Pat. No. 8,692,927; U.S. Pat. No. 8,695,880;
U.S. Pat. No. 8,698,949; U.S. Pat. No. 8,717,494;
U.S. Pat. No. 8,717,494; U.S. Pat. No. 8,720,783;
U.S. Pat. No. 8,723,804; U.S. Pat. No. 8,723,904;
U.S. Pat. No. 8,727,223; U.S. Pat. No. D702,237;
U.S. Pat. No. 8,740,082; U.S. Pat. No. 8,740,085;
U.S. Pat. No. 8,746,563; U.S. Pat. No. 8,750,445;
U.S. Pat. No. 8,752,766; U.S. Pat. No. 8,756,059;
U.S. Pat. No. 8,757,495; U.S. Pat. No. 8,760,563;
U.S. Pat. No. 8,763,909; U.S. Pat. No. 8,777,108;
U.S. Pat. No. 8,777,109; U.S. Pat. No. 8,779,898;
U.S. Pat. No. 8,781,520; U.S. Pat. No. 8,783,573;
U.S. Pat. No. 8,789,757; U.S. Pat. No. 8,789,758;
U.S. Pat. No. 8,789,759; U.S. Pat. No. 8,794,520;
U.S. Pat. No. 8,794,522; U.S. Pat. No. 8,794,525;
U.S. Pat. No. 8,794,526; U.S. Pat. No. 8,798,367;
U.S. Pat. No. 8,807,431; U.S. Pat. No. 8,807,432;
U.S. Pat. No. 8,820,630; U.S. Pat. No. 8,822,848;
U.S. Pat. No. 8,824,692; U.S. Pat. No. 8,824,696;
U.S. Pat. No. 8,842,849; U.S. Pat. No. 8,844,822;
U.S. Pat. No. 8,844,823; U.S. Pat. No. 8,849,019;
U.S. Pat. No. 8,851,383; U.S. Pat. No. 8,854,633;
U.S. Pat. No. 8,866,963; U.S. Pat. No. 8,868,421;
U.S. Pat. No. 8,868,519; U.S. Pat. No. 8,868,802;
U.S. Pat. No. 8,868,803; U.S. Pat. No. 8,870,074;
U.S. Pat. No. 8,879,639; U.S. Pat. No. 8,880,426;
U.S. Pat. No. 8,881,983; U.S. Pat. No. 8,881,987;
U.S. Pat. No. 8,903,172; U.S. Pat. No. 8,908,995;
U.S. Pat. No. 8,910,870; U.S. Pat. No. 8,910,875;
U.S. Pat. No. 8,914,290; U.S. Pat. No. 8,914,788;
U.S. Pat. No. 8,915,439; U.S. Pat. No. 8,915,444;
U.S. Pat. No. 8,916,789; U.S. Pat. No. 8,918,250;
U.S. Pat. No. 8,918,564; U.S. Pat. No. 8,925,818;
U.S. Pat. No. 8,939,374; U.S. Pat. No. 8,942,480;
U.S. Pat. No. 8,944,313; U.S. Pat. No. 8,944,327;
U.S. Pat. No. 8,944,332; U.S. Pat. No. 8,950,678;
U.S. Pat. No. 8,967,468; U.S. Pat. No. 8,971,346;
U.S. Pat. No. 8,976,030; U.S. Pat. No. 8,976,368;
U.S. Pat. No. 8,978,981; U.S. Pat. No. 8,978,983;
U.S. Pat. No. 8,978,984; U.S. Pat. No. 8,985,456;
U.S. Pat. No. 8,985,457; U.S. Pat. No. 8,985,459;
U.S. Pat. No. 8,985,461; U.S. Pat. No. 8,988,578;
U.S. Pat. No. 8,988,590; U.S. Pat. No. 8,991,704;
U.S. Pat. No. 8,996,194; U.S. Pat. No. 8,996,384;
U.S. Pat. No. 9,002,641; U.S. Pat. No. 9,007,368;
U.S. Pat. No. 9,010,641; U.S. Pat. No. 9,015,513;
U.S. Pat. No. 9,016,576; U.S. Pat. No. 9,022,288;
U.S. Pat. No. 9,030,964; U.S. Pat. No. 9,033,240;
U.S. Pat. No. 9,033,242; U.S. Pat. No. 9,036,054;
U.S. Pat. No. 9,037,344; U.S. Pat. No. 9,038,911;
U.S. Pat. No. 9,038,915; U.S. Pat. No. 9,047,098;
U.S. Pat. No. 9,047,359; U.S. Pat. No. 9,047,420;
U.S. Pat. No. 9,047,525; U.S. Pat. No. 9,047,531;
U.S. Pat. No. 9,053,055; U.S. Pat. No. 9,053,378;
U.S. Pat. No. 9,053,380; U.S. Pat. No. 9,058,526;
U.S. Pat. No. 9,064,165; U.S. Pat. No. 9,064,167;
U.S. Pat. No. 9,064,168; U.S. Pat. No. 9,064,254;
U.S. Pat. No. 9,066,032; U.S. Pat. No. 9,070,032;
U.S. Design Pat. No. D716,285;
U.S. Design Pat. No. D723,560;
U.S. Design Pat. No. D730,357;
U.S. Design Pat. No. D730,901;
U.S. Design Pat. No. D730,902;
U.S. Design Pat. No. D733,112;
U.S. Design Pat. No. D734,339;
International Publication No. 2013/163789;
International Publication No. 2013/173985;
International Publication No. 2014/019130;
International Publication No. 2014/110495;
U.S. Patent Application Publication No. 2008/0185432;
U.S. Patent Application Publication No. 2009/0134221;
U.S. Patent Application Publication No. 2010/0177080;
U.S. Patent Application Publication No. 2010/0177076;
U.S. Patent Application Publication No. 2010/0177707;
U.S. Patent Application Publication No. 2010/0177749;
U.S. Patent Application Publication No. 2010/0265880;
U.S. Patent Application Publication No. 2011/0202554;
U.S. Patent Application Publication No. 2012/0111946;
U.S. Patent Application Publication No. 2012/0168511;
U.S. Patent Application Publication No. 2012/0168512;
U.S. Patent Application Publication No. 2012/0193423;
U.S. Patent Application Publication No. 2012/0203647;
U.S. Patent Application Publication No. 2012/0223141;
U.S. Patent Application Publication No. 2012/0228382;
U.S. Patent Application Publication No. 2012/0248188;
U.S. Patent Application Publication No. 2013/0043312;
U.S. Patent Application Publication No. 2013/0082104;
U.S. Patent Application Publication No. 2013/0175341;
U.S. Patent Application Publication No. 2013/0175343;
U.S. Patent Application Publication No. 2013/0257744;
U.S. Patent Application Publication No. 2013/0257759;
U.S. Patent Application Publication No. 2013/0270346;
U.S. Patent Application Publication No. 2013/0287258;
U.S. Patent Application Publication No. 2013/0292475;
U.S. Patent Application Publication No. 2013/0292477;
U.S. Patent Application Publication No. 2013/0293539;
U.S. Patent Application Publication No. 2013/0293540;
U.S. Patent Application Publication No. 2013/0306728;
U.S. Patent Application Publication No. 2013/0306731;
U.S. Patent Application Publication No. 2013/0307964;

U.S. Patent Application Publication No. 2013/0308625;
U.S. Patent Application Publication No. 2013/0313324;
U.S. Patent Application Publication No. 2013/0313325;
U.S. Patent Application Publication No. 2013/0342717;
U.S. Patent Application Publication No. 2014/0001267;
U.S. Patent Application Publication No. 2014/0008439;
U.S. Patent Application Publication No. 2014/0025584;
U.S. Patent Application Publication No. 2014/0034734;
U.S. Patent Application Publication No. 2014/0036848;
U.S. Patent Application Publication No. 2014/0039693;
U.S. Patent Application Publication No. 2014/0042814;
U.S. Patent Application Publication No. 2014/0049120;
U.S. Patent Application Publication No. 2014/0049635;
U.S. Patent Application Publication No. 2014/0061306;
U.S. Patent Application Publication No. 2014/0063289;
U.S. Patent Application Publication No. 2014/0066136;
U.S. Patent Application Publication No. 2014/0067692;
U.S. Patent Application Publication No. 2014/0070005;
U.S. Patent Application Publication No. 2014/0071840;
U.S. Patent Application Publication No. 2014/0074746;
U.S. Patent Application Publication No. 2014/0076974;
U.S. Patent Application Publication No. 2014/0078341;
U.S. Patent Application Publication No. 2014/0078345;
U.S. Patent Application Publication No. 2014/0097249;
U.S. Patent Application Publication No. 2014/0098792;
U.S. Patent Application Publication No. 2014/0100813;
U.S. Patent Application Publication No. 2014/0103115;
U.S. Patent Application Publication No. 2014/0104413;
U.S. Patent Application Publication No. 2014/0104414;
U.S. Patent Application Publication No. 2014/0104416;
U.S. Patent Application Publication No. 2014/0104451;
U.S. Patent Application Publication No. 2014/0106594;
U.S. Patent Application Publication No. 2014/0106725;
U.S. Patent Application Publication No. 2014/0108010;
U.S. Patent Application Publication No. 2014/0108402;
U.S. Patent Application Publication No. 2014/0110485;
U.S. Patent Application Publication No. 2014/0114530;
U.S. Patent Application Publication No. 2014/0124577;
U.S. Patent Application Publication No. 2014/0124579;
U.S. Patent Application Publication No. 2014/0125842;
U.S. Patent Application Publication No. 2014/0125853;
U.S. Patent Application Publication No. 2014/0125999;
U.S. Patent Application Publication No. 2014/0129378;
U.S. Patent Application Publication No. 2014/0131438;
U.S. Patent Application Publication No. 2014/0131441;
U.S. Patent Application Publication No. 2014/0131443;
U.S. Patent Application Publication No. 2014/0131444;
U.S. Patent Application Publication No. 2014/0131445;
U.S. Patent Application Publication No. 2014/0131448;
U.S. Patent Application Publication No. 2014/0133379;
U.S. Patent Application Publication No. 2014/0136208;
U.S. Patent Application Publication No. 2014/0140585;
U.S. Patent Application Publication No. 2014/0151453;
U.S. Patent Application Publication No. 2014/0152882;
U.S. Patent Application Publication No. 2014/0158770;
U.S. Patent Application Publication No. 2014/0159869;
U.S. Patent Application Publication No. 2014/0166755;
U.S. Patent Application Publication No. 2014/0166759;
U.S. Patent Application Publication No. 2014/0168787;
U.S. Patent Application Publication No. 2014/0175165;
U.S. Patent Application Publication No. 2014/0175172;
U.S. Patent Application Publication No. 2014/0191644;
U.S. Patent Application Publication No. 2014/0191913;
U.S. Patent Application Publication No. 2014/0197238;
U.S. Patent Application Publication No. 2014/0197239;
U.S. Patent Application Publication No. 2014/0197304;
U.S. Patent Application Publication No. 2014/0214631;
U.S. Patent Application Publication No. 2014/0217166;
U.S. Patent Application Publication No. 2014/0217180;
U.S. Patent Application Publication No. 2014/0231500;
U.S. Patent Application Publication No. 2014/0232930;
U.S. Patent Application Publication No. 2014/0247315;
U.S. Patent Application Publication No. 2014/0263493;
U.S. Patent Application Publication No. 2014/0263645;
U.S. Patent Application Publication No. 2014/0267609;
U.S. Patent Application Publication No. 2014/0270196;
U.S. Patent Application Publication No. 2014/0270229;
U.S. Patent Application Publication No. 2014/0278387;
U.S. Patent Application Publication No. 2014/0278391;
U.S. Patent Application Publication No. 2014/0282210;
U.S. Patent Application Publication No. 2014/0284384;
U.S. Patent Application Publication No. 2014/0288933;
U.S. Patent Application Publication No. 2014/0297058;
U.S. Patent Application Publication No. 2014/0299665;
U.S. Patent Application Publication No. 2014/0312121;
U.S. Patent Application Publication No. 2014/0319220;
U.S. Patent Application Publication No. 2014/0319221;
U.S. Patent Application Publication No. 2014/0326787;
U.S. Patent Application Publication No. 2014/0332590;
U.S. Patent Application Publication No. 2014/0344943;
U.S. Patent Application Publication No. 2014/0346233;
U.S. Patent Application Publication No. 2014/0351317;
U.S. Patent Application Publication No. 2014/0353373;
U.S. Patent Application Publication No. 2014/0361073;
U.S. Patent Application Publication No. 2014/0361082;
U.S. Patent Application Publication No. 2014/0362184;
U.S. Patent Application Publication No. 2014/0363015;
U.S. Patent Application Publication No. 2014/0369511;
U.S. Patent Application Publication No. 2014/0374483;
U.S. Patent Application Publication No. 2014/0374485;
U.S. Patent Application Publication No. 2015/0001301;
U.S. Patent Application Publication No. 2015/0001304;
U.S. Patent Application Publication No. 2015/0003673;
U.S. Patent Application Publication No. 2015/0009338;
U.S. Patent Application Publication No. 2015/0009610;
U.S. Patent Application Publication No. 2015/0014416;
U.S. Patent Application Publication No. 2015/0021397;
U.S. Patent Application Publication No. 2015/0028102;
U.S. Patent Application Publication No. 2015/0028103;
U.S. Patent Application Publication No. 2015/0028104;
U.S. Patent Application Publication No. 2015/0029002;
U.S. Patent Application Publication No. 2015/0032709;
U.S. Patent Application Publication No. 2015/0039309;
U.S. Patent Application Publication No. 2015/0039878;
U.S. Patent Application Publication No. 2015/0040378;
U.S. Patent Application Publication No. 2015/0048168;
U.S. Patent Application Publication No. 2015/0049347;
U.S. Patent Application Publication No. 2015/0051992;
U.S. Patent Application Publication No. 2015/0053766;
U.S. Patent Application Publication No. 2015/0053768;
U.S. Patent Application Publication No. 2015/0053769;
U.S. Patent Application Publication No. 2015/0060544;
U.S. Patent Application Publication No. 2015/0062366;
U.S. Patent Application Publication No. 2015/0063215;
U.S. Patent Application Publication No. 2015/0063676;
U.S. Patent Application Publication No. 2015/0069130;
U.S. Patent Application Publication No. 2015/0071819;
U.S. Patent Application Publication No. 2015/0083800;
U.S. Patent Application Publication No. 2015/0086114;
U.S. Patent Application Publication No. 2015/0088522;
U.S. Patent Application Publication No. 2015/0096872;
U.S. Patent Application Publication No. 2015/0099557;
U.S. Patent Application Publication No. 2015/0100196;
U.S. Patent Application Publication No. 2015/0102109;

U.S. Patent Application Publication No. 2015/0115035;
U.S. Patent Application Publication No. 2015/0127791;
U.S. Patent Application Publication No. 2015/0128116;
U.S. Patent Application Publication No. 2015/0129659;
U.S. Patent Application Publication No. 2015/0133047;
U.S. Patent Application Publication No. 2015/0134470;
U.S. Patent Application Publication No. 2015/0136851;
U.S. Patent Application Publication No. 2015/0136854;
U.S. Patent Application Publication No. 2015/0142492;
U.S. Patent Application Publication No. 2015/0144692;
U.S. Patent Application Publication No. 2015/0144698;
U.S. Patent Application Publication No. 2015/0144701;
U.S. Patent Application Publication No. 2015/0149946;
U.S. Patent Application Publication No. 2015/0161429;
U.S. Patent Application Publication No. 2015/0169925;
U.S. Patent Application Publication No. 2015/0169929;
U.S. Patent Application Publication No. 2015/0178523;
U.S. Patent Application Publication No. 2015/0178534;
U.S. Patent Application Publication No. 2015/0178535;
U.S. Patent Application Publication No. 2015/0178536;
U.S. Patent Application Publication No. 2015/0178537;
U.S. Patent Application Publication No. 2015/0181093;
U.S. Patent Application Publication No. 2015/0181109;
U.S. patent application Ser. No. 13/367,978 for a Laser Scanning Module Employing an Elastomeric U-Hinge Based Laser Scanning Assembly, filed Feb. 7, 2012 (Feng et al.);
U.S. patent application Ser. No. 29/458,405 for an Electronic Device, filed Jun. 19, 2013 (Fitch et al.);
U.S. patent application Ser. No. 29/459,620 for an Electronic Device Enclosure, filed Jul. 2, 2013 (London et al.);
U.S. patent application Ser. No. 29/468,118 for an Electronic Device Case, filed Sep. 26, 2013 (Oberpriller et al.);
U.S. patent application Ser. No. 14/150,393 for Indicia-reader Having Unitary Construction Scanner, filed Jan. 8, 2014 (Colavito et al.);
U.S. patent application Ser. No. 14/200,405 for Indicia Reader for Size-Limited Applications filed Mar. 7, 2014 (Feng et al.);
U.S. patent application Ser. No. 14/231,898 for Hand-Mounted Indicia-Reading Device with Finger Motion Triggering filed Apr. 1, 2014 (Van Horn et al.);
U.S. patent application Ser. No. 29/486,759 for an Imaging Terminal, filed Apr. 2, 2014 (Oberpriller et al.);
U.S. patent application Ser. No. 14/257,364 for Docking System and Method Using Near Field Communication filed Apr. 21, 2014 (Showering);
U.S. patent application Ser. No. 14/264,173 for Autofocus Lens System for Indicia Readers filed Apr. 29, 2014 (Ackley et al.);
U.S. patent application Ser. No. 14/277,337 for MULTIPURPOSE OPTICAL READER, filed May 14, 2014 (Jovanovski et al.);
U.S. patent application Ser. No. 14/283,282 for TERMINAL HAVING ILLUMINATION AND FOCUS CONTROL filed May 21, 2014 (Liu et al.);
U.S. patent application Ser. No. 14/327,827 for a MOBILE-PHONE ADAPTER FOR ELECTRONIC TRANSACTIONS, filed Jul. 10, 2014 (Hejl);
U.S. patent application Ser. No. 14/334,934 for a SYSTEM AND METHOD FOR INDICIA VERIFICATION, filed Jul. 18, 2014 (Hejl);
U.S. patent application Ser. No. 14/339,708 for LASER SCANNING CODE SYMBOL READING SYSTEM, filed Jul. 24, 2014 (Xian et al.);
U.S. patent application Ser. No. 14/340,627 for an AXIALLY REINFORCED FLEXIBLE SCAN ELEMENT, filed Jul. 25, 2014 (Rueblinger et al.);
U.S. patent application Ser. No. 14/446,391 for MULTIFUNCTION POINT OF SALE APPARATUS WITH OPTICAL SIGNATURE CAPTURE filed Jul. 30, 2014 (Good et al.);
U.S. patent application Ser. No. 14/452,697 for INTERACTIVE INDICIA READER, filed Aug. 6, 2014 (Todeschini);
U.S. patent application Ser. No. 14/453,019 for DIMENSIONING SYSTEM WITH GUIDED ALIGNMENT, filed Aug. 6, 2014 (Li et al.);
U.S. patent application Ser. No. 14/462,801 for MOBILE COMPUTING DEVICE WITH DATA COGNITION SOFTWARE, filed on Aug. 19, 2014 (Todeschini et al.);
U.S. patent application Ser. No. 14/483,056 for VARIABLE DEPTH OF FIELD BARCODE SCANNER filed Sep. 10, 2014 (McCloskey et al.);
U.S. patent application Ser. No. 14/513,808 for IDENTIFYING INVENTORY ITEMS IN A STORAGE FACILITY filed Oct. 14, 2014 (Singel et al.);
U.S. patent application Ser. No. 14/519,195 for HANDHELD DIMENSIONING SYSTEM WITH FEEDBACK filed Oct. 21, 2014 (Laffargue et al.);
U.S. patent application Ser. No. 14/519,179 for DIMENSIONING SYSTEM WITH MULTIPATH INTERFERENCE MITIGATION filed Oct. 21, 2014 (Thuries et al.);
U.S. patent application Ser. No. 14/519,211 for SYSTEM AND METHOD FOR DIMENSIONING filed Oct. 21, 2014 (Ackley et al.);
U.S. patent application Ser. No. 14/519,233 for HANDHELD DIMENSIONER WITH DATA-QUALITY INDICATION filed Oct. 21, 2014 (Laffargue et al.);
U.S. patent application Ser. No. 14/519,249 for HANDHELD DIMENSIONING SYSTEM WITH MEASUREMENT-CONFORMANCE FEEDBACK filed Oct. 21, 2014 (Ackley et al.);
U.S. patent application Ser. No. 14/527,191 for METHOD AND SYSTEM FOR RECOGNIZING SPEECH USING WILDCARDS IN AN EXPECTED RESPONSE filed Oct. 29, 2014 (Braho et al.);
U.S. patent application Ser. No. 14/529,563 for ADAPTABLE INTERFACE FOR A MOBILE COMPUTING DEVICE filed Oct. 31, 2014 (Schoon et al.);
U.S. patent application Ser. No. 14/529,857 for BARCODE READER WITH SECURITY FEATURES filed Oct. 31, 2014 (Todeschini et al.);
U.S. patent application Ser. No. 14/398,542 for PORTABLE ELECTRONIC DEVICES HAVING A SEPARATE LOCATION TRIGGER UNIT FOR USE IN CONTROLLING AN APPLICATION UNIT filed Nov. 3, 2014 (Bian et al.);
U.S. patent application Ser. No. 14/531,154 for DIRECTING AN INSPECTOR THROUGH AN INSPECTION filed Nov. 3, 2014 (Miller et al.);
U.S. patent application Ser. No. 14/533,319 for BARCODE SCANNING SYSTEM USING WEARABLE DEVICE WITH EMBEDDED CAMERA filed Nov. 5, 2014 (Todeschini);
U.S. patent application Ser. No. 14/535,764 for CONCATENATED EXPECTED RESPONSES FOR SPEECH RECOGNITION filed Nov. 7, 2014 (Braho et al.);
U.S. patent application Ser. No. 14/568,305 for AUTO-CONTRAST VIEWFINDER FOR AN INDICIA READER filed Dec. 12, 2014 (Todeschini);

U.S. patent application Ser. No. 14/573,022 for DYNAMIC DIAGNOSTIC INDICATOR GENERATION filed Dec. 17, 2014 (Goldsmith);

U.S. patent application Ser. No. 14/578,627 for SAFETY SYSTEM AND METHOD filed Dec. 22, 2014 (Ackley et al.);

U.S. patent application Ser. No. 14/580,262 for MEDIA GATE FOR THERMAL TRANSFER PRINTERS filed Dec. 23, 2014 (Bowles);

U.S. patent application Ser. No. 14/590,024 for SHELVING AND PACKAGE LOCATING SYSTEMS FOR DELIVERY VEHICLES filed Jan. 6, 2015 (Payne);

U.S. patent application Ser. No. 14/596,757 for SYSTEM AND METHOD FOR DETECTING BARCODE PRINTING ERRORS filed Jan. 14, 2015 (Ackley);

U.S. patent application Ser. No. 14/416,147 for OPTICAL READING APPARATUS HAVING VARIABLE SETTINGS filed Jan. 21, 2015 (Chen et al.);

U.S. patent application Ser. No. 14/614,706 for DEVICE FOR SUPPORTING AN ELECTRONIC TOOL ON A USER'S HAND filed Feb. 5, 2015 (Oberpriller et al.);

U.S. patent application Ser. No. 14/614,796 for CARGO APPORTIONMENT TECHNIQUES filed Feb. 5, 2015 (Morton et al.);

U.S. patent application Ser. No. 29/516,892 for TABLE COMPUTER filed Feb. 6, 2015 (Bidwell et al.);

U.S. patent application Ser. No. 14/619,093 for METHODS FOR TRAINING A SPEECH RECOGNITION SYSTEM filed Feb. 11, 2015 (Pecorari);

U.S. patent application Ser. No. 14/628,708 for DEVICE, SYSTEM, AND METHOD FOR DETERMINING THE STATUS OF CHECKOUT LANES filed Feb. 23, 2015 (Todeschini);

U.S. patent application Ser. No. 14/630,841 for TERMINAL INCLUDING IMAGING ASSEMBLY filed Feb. 25, 2015 (Gomez et al.);

U.S. patent application Ser. No. 14/635,346 for SYSTEM AND METHOD FOR RELIABLE STORE-AND-FORWARD DATA HANDLING BY ENCODED INFORMATION READING TERMINALS filed Mar. 2, 2015 (Sevier);

U.S. patent application Ser. No. 29/519,017 for SCANNER filed Mar. 2, 2015 (Zhou et al.);

U.S. patent application Ser. No. 14/405,278 for DESIGN PATTERN FOR SECURE STORE filed Mar. 9, 2015 (Zhu et al.);

U.S. patent application Ser. No. 14/660,970 for DECODABLE INDICIA READING TERMINAL WITH COMBINED ILLUMINATION filed Mar. 18, 2015 (Kearney et al.);

U.S. patent application Ser. No. 14/661,013 for REPROGRAMMING SYSTEM AND METHOD FOR DEVICES INCLUDING PROGRAMMING SYMBOL filed Mar. 18, 2015 (Soule et al.);

U.S. patent application Ser. No. 14/662,922 for MULTIFUNCTION POINT OF SALE SYSTEM filed Mar. 19, 2015 (Van Horn et al.);

U.S. patent application Ser. No. 14/663,638 for VEHICLE MOUNT COMPUTER WITH CONFIGURABLE IGNITION SWITCH BEHAVIOR filed Mar. 20, 2015 (Davis et al.);

U.S. patent application Ser. No. 14/664,063 for METHOD AND APPLICATION FOR SCANNING A BARCODE WITH A SMART DEVICE WHILE CONTINUOUSLY RUNNING AND DISPLAYING AN APPLICATION ON THE SMART DEVICE DISPLAY filed Mar. 20, 2015 (Todeschini);

U.S. patent application Ser. No. 14/669,280 for TRANSFORMING COMPONENTS OF A WEB PAGE TO VOICE PROMPTS filed Mar. 26, 2015 (Funyak et al.);

U.S. patent application Ser. No. 14/674,329 for AIMER FOR BARCODE SCANNING filed Mar. 31, 2015 (Bidwell);

U.S. patent application Ser. No. 14/676,109 for INDICIA READER filed Apr. 1, 2015 (Huck);

U.S. patent application Ser. No. 14/676,327 for DEVICE MANAGEMENT PROXY FOR SECURE DEVICES filed Apr. 1, 2015 (Yeakley et al.);

U.S. patent application Ser. No. 14/676,898 for NAVIGATION SYSTEM CONFIGURED TO INTEGRATE MOTION SENSING DEVICE INPUTS filed Apr. 2, 2015 (Showering);

U.S. patent application Ser. No. 14/679,275 for DIMENSIONING SYSTEM CALIBRATION SYSTEMS AND METHODS filed Apr. 6, 2015 (Laffargue et al.);

U.S. patent application Ser. No. 29/523,098 for HANDLE FOR A TABLET COMPUTER filed Apr. 7, 2015 (Bidwell et al.);

U.S. patent application Ser. No. 14/682,615 for SYSTEM AND METHOD FOR POWER MANAGEMENT OF MOBILE DEVICES filed Apr. 9, 2015 (Murawski et al.);

U.S. patent application Ser. No. 14/686,822 for MULTIPLE PLATFORM SUPPORT SYSTEM AND METHOD filed Apr. 15, 2015 (Qu et al.);

U.S. patent application Ser. No. 14/687,289 for SYSTEM FOR COMMUNICATION VIA A PERIPHERAL HUB filed Apr. 15, 2015 (Kohtz et al.);

U.S. patent application Ser. No. 29/524,186 for SCANNER filed Apr. 17, 2015 (Zhou et al.);

U.S. patent application Ser. No. 14/695,364 for MEDICATION MANAGEMENT SYSTEM filed Apr. 24, 2015 (Sewell et al.);

U.S. patent application Ser. No. 14/695,923 for SECURE UNATTENDED NETWORK AUTHENTICATION filed Apr. 24, 2015 (Kubler et al.);

U.S. patent application Ser. No. 29/525,068 for TABLET COMPUTER WITH REMOVABLE SCANNING DEVICE filed Apr. 27, 2015 (Schulte et al.);

U.S. patent application Ser. No. 14/699,436 for SYMBOL READING SYSTEM HAVING PREDICTIVE DIAGNOSTICS filed Apr. 29, 2015 (Nahill et al.);

U.S. patent application Ser. No. 14/702,110 for SYSTEM AND METHOD FOR REGULATING BARCODE DATA INJECTION INTO A RUNNING APPLICATION ON A SMART DEVICE filed May 1, 2015 (Todeschini et al.);

U.S. patent application Ser. No. 14/702,979 for TRACKING BATTERY CONDITIONS filed May 4, 2015 (Young et al.);

U.S. patent application Ser. No. 14/704,050 for INTERMEDIATE LINEAR POSITIONING filed May 5, 2015 (Charpentier et al.);

U.S. patent application Ser. No. 14/705,012 for HANDS-FREE HUMAN MACHINE INTERFACE RESPONSIVE TO A DRIVER OF A VEHICLE filed May 6, 2015 (Fitch et al.);

U.S. patent application Ser. No. 14/705,407 for METHOD AND SYSTEM TO PROTECT SOFTWARE-BASED NETWORK-CONNECTED DEVICES FROM ADVANCED PERSISTENT THREAT filed May 6, 2015 (Hussey et al.);

U.S. patent application Ser. No. 14/707,037 for SYSTEM AND METHOD FOR DISPLAY OF INFORMATION USING A VEHICLE-MOUNT COMPUTER filed May 8, 2015 (Chamberlin);

U.S. patent application Ser. No. 14/707,123 for APPLICATION INDEPENDENT DEX/UCS INTERFACE filed May 8, 2015 (Pape);

U.S. patent application Ser. No. 14/707,492 for METHOD AND APPARATUS FOR READING OPTICAL INDICIA USING A PLURALITY OF DATA SOURCES filed May 8, 2015 (Smith et al.);

U.S. patent application Ser. No. 14/710,666 for PRE-PAID USAGE SYSTEM FOR ENCODED INFORMATION READING TERMINALS filed May 13, 2015 (Smith);

U.S. patent application Ser. No. 29/526,918 for CHARGING BASE filed May 14, 2015 (Fitch et al.);

U.S. patent application Ser. No. 14/715,672 for AUGMENTED REALITY ENABLED HAZARD DISPLAY filed May 19, 2015 (Venkatesha et al.);

U.S. patent application Ser. No. 14/715,916 for EVALUATING IMAGE VALUES filed May 19, 2015 (Ackley);

U.S. patent application Ser. No. 14/722,608 for INTERACTIVE USER INTERFACE FOR CAPTURING A DOCUMENT IN AN IMAGE SIGNAL filed May 27, 2015 (Showering et al.);

U.S. patent application Ser. No. 29/528,165 for IN-COUNTER BARCODE SCANNER filed May 27, 2015 (Oberpriller et al.);

U.S. patent application Ser. No. 14/724,134 for ELECTRONIC DEVICE WITH WIRELESS PATH SELECTION CAPABILITY filed May 28, 2015 (Wang et al.);

U.S. patent application Ser. No. 14/724,849 for METHOD OF PROGRAMMING THE DEFAULT CABLE INTERFACE SOFTWARE IN AN INDICIA READING DEVICE filed May 29, 2015 (Barten);

U.S. patent application Ser. No. 14/724,908 for IMAGING APPARATUS HAVING IMAGING ASSEMBLY filed May 29, 2015 (Barber et al.);

U.S. patent application Ser. No. 14/725,352 for APPARATUS AND METHODS FOR MONITORING ONE OR MORE PORTABLE DATA TERMINALS (Caballero et al.);

U.S. patent application Ser. No. 29/528,590 for ELECTRONIC DEVICE filed May 29, 2015 (Fitch et al.);

U.S. patent application Ser. No. 29/528,890 for MOBILE COMPUTER HOUSING filed Jun. 2, 2015 (Fitch et al.);

U.S. patent application Ser. No. 14/728,397 for DEVICE MANAGEMENT USING VIRTUAL INTERFACES CROSS-REFERENCE TO RELATED APPLICATIONS filed Jun. 2, 2015 (Caballero);

U.S. patent application Ser. No. 14/732,870 for DATA COLLECTION MODULE AND SYSTEM filed Jun. 8, 2015 (Powilleit);

U.S. patent application Ser. No. 29/529,441 for INDICIA READING DEVICE filed Jun. 8, 2015 (Zhou et al.);

U.S. patent application Ser. No. 14/735,717 for INDICIA-READING SYSTEMS HAVING AN INTERFACE WITH A USER'S NERVOUS SYSTEM filed Jun. 10, 2015 (Todeschini);

U.S. patent application Ser. No. 14/738,038 for METHOD OF AND SYSTEM FOR DETECTING OBJECT WEIGHING INTERFERENCES filed Jun. 12, 2015 (Amundsen et al.);

U.S. patent application Ser. No. 14/740,320 for TACTILE SWITCH FOR A MOBILE ELECTRONIC DEVICE filed Jun. 16, 2015 (Bandringa);

U.S. patent application Ser. No. 14/740,373 for CALIBRATING A VOLUME DIMENSIONER filed Jun. 16, 2015 (Ackley et al.);

U.S. patent application Ser. No. 14/742,818 for INDICIA READING SYSTEM EMPLOYING DIGITAL GAIN CONTROL filed Jun. 18, 2015 (Xian et al.);

U.S. patent application Ser. No. 14/743,257 for WIRELESS MESH POINT PORTABLE DATA TERMINAL filed Jun. 18, 2015 (Wang et al.);

U.S. patent application Ser. No. 29/530,600 for CYCLONE filed Jun. 18, 2015 (Vargo et al);

U.S. patent application Ser. No. 14/744,633 for IMAGING APPARATUS COMPRISING IMAGE SENSOR ARRAY HAVING SHARED GLOBAL SHUTTER CIRCUITRY filed Jun. 19, 2015 (Wang);

U.S. patent application Ser. No. 14/744,836 for CLOUD-BASED SYSTEM FOR READING OF DECODABLE INDICIA filed Jun. 19, 2015 (Todeschini et al.);

U.S. patent application Ser. No. 14/745,006 for SELECTIVE OUTPUT OF DECODED MESSAGE DATA filed Jun. 19, 2015 (Todeschini et al.);

U.S. patent application Ser. No. 14/747,197 for OPTICAL PATTERN PROJECTOR filed Jun. 23, 2015 (Thuries et al.);

U.S. patent application Ser. No. 14/747,490 for DUAL-PROJECTOR THREE-DIMENSIONAL SCANNER filed Jun. 23, 2015 (Jovanovski et al.); and U.S. patent application Ser. No. 14/748,446 for CORDLESS INDICIA READER WITH A MULTIFUNCTION COIL FOR WIRELESS CHARGING AND EAS DEACTIVATION, filed Jun. 24, 2015 (Xie et al.).

In the specification and/or figures, typical embodiments of the invention have been disclosed. The present invention is not limited to such exemplary embodiments. The use of the term "and/or" includes any and all combinations of one or more of the associated listed items. The figures are schematic representations and so are not necessarily drawn to scale. Unless otherwise noted, specific terms have been used in a generic and descriptive sense and not for purposes of limitation.

The invention claimed is:

1. A printer, comprising:
a light source configured to direct light toward a print medium path;
a red-green-blue (RGB) light sensor configured to receive light from the light source reflected by a print medium in the print medium path;
an infrared light filter situated between the RGB light sensor and the print medium path, the infrared light filter configured to filter infrared light from entering the RGB light sensor; and
a processor communicatively coupled to the RGB light sensor, the processor configured to:
detect at least one form element of a print medium based at least in part on an output signal from the RGB light sensor;
retrieve a stored electronic representation of a form based at least in part on the at least one form element;
match the at least one form element to a stored electronic representation of the form;
identify one or more locations of the print medium for printing based at least in part on the match; and
cause the printer to print to the one or more locations of the print medium.

2. The printer according to claim 1, wherein the one or more locations of the print medium comprises a beginning of the form.

3. The printer according to claim 1, further comprising an I2C interface between the RGB sensor and the processor.

4. The printer according to claim 1, where the at least one form element comprises at least one cell designated for bounding data to be printed.

5. The printer according to claim 1, where the processor is configured to:
- advance the print medium through the printer;
- identify form elements in the output from the RGB light sensor as the print medium is being advanced through the printer; and
- store the identified form elements to memory as an electronic representation of the form.

6. The printer according to claim 1, where the processor is configured to determine that the printer is out of media by detecting light intensity below a specified threshold.

7. The printer according to claim 1, where the processor is configured to determine that the printer contains print media by detecting light intensity greater than a specified threshold.

8. A method of printing to a print medium, the method comprising:
- advancing a print medium through a printer, the advancing print medium following a print medium path;
- receiving an output signal from a red-green-blue (RGB) light sensor, the output signal corresponding to light from a light source reflected by the print medium, the light source configured to direct light towards the print medium in the print medium path;
- detecting at least one form element of the print medium based at least in part on the output signal;
- retrieving a stored electronic representation of a form based at least in part on the at least one form element;
- matching the at least one form element to the stored electronic representation of the form;
- identifying one or more locations of the print medium for printing based at least on part on the match; and
- printing to the one or more locations of the print medium.

9. The method according to claim 8, comprising filtering infrared light out of light that is passed to the RGB light sensor.

10. The method according to claim 8, where the output signal from the RGB sensor is passed to a processor using an I2C interface.

11. The method according to claim 8, where the at least one form element comprises at least one cell designated for bounding data to be printed.

12. The method according to claim 8, comprising an initialization comprising:
- advancing the print medium through the printer;
- identifying form elements in the output from the RGB light sensor as the print medium is being advanced through the printer; and
- storing the identified form elements to memory as an electronic representation of the form.

13. The method according to claim 8, comprising detecting light intensity and determining that the printer is out of media by detecting light intensity below a specified threshold.

14. The method according to claim 8, comprising detecting light intensity and determining the printer contains print medium by detecting light intensity greater than a specified threshold.

15. The method according to claim 8, comprising storing a dot count representing a number of lines of the print medium as a measure of location along the form where a form element is situated.

16. A method of printing to a form, the method comprising:
- advancing a first form through a printer;
- receiving a first output signal from a red-green-blue (RGB) light sensor, the first output signal corresponding to light from a light source reflected by the first form;
- identifying one or elements of the first form based at least in part on the first output signal;
- storing the one or more elements to memory as an electronic representation of the first form;
- advancing a second form through the printer;
- receiving a second output signal from the RGB light sensor, the second output signal corresponding to light from the light source reflected by the second form;
- detecting at least one element of the second form based at least in part on the second output signal;
- matching the at least one element of the second form to the electronic representation of the first form;
- identifying one or more locations of the second form for printing based at least on part on the matching; and
- printing to the one or more locations of the second form.

17. The method of claim 16, wherein the one or more locations of the second form comprise a beginning of the second form.

18. The method of claim 16, wherein the one or more elements of the first form comprise a cell designated for bounding data to be printed, and/or wherein the one or more locations of the second form comprise a cell designated for bounding data to be printed.

19. The method of claim 16, wherein the first form and/or the second form comprises printing medium for parking violation citations.

20. The method of claim 16, wherein the first form and/or the second form comprises a label.

* * * * *